United States Patent
Tallon et al.

(10) Patent No.: US 11,912,831 B2
(45) Date of Patent: Feb. 27, 2024

(54) HYDROXYETHYLPYRROLIDONE ETHACRYLATE/GLYCIDYL ETHACRYLATE COPOLYMERS

(71) Applicant: ISP INVESTMENTS LLC, Wilmington, DE (US)

(72) Inventors: Michael A Tallon, Aberdeen, NJ (US); Alaa Alharizah, Dover, NJ (US)

(73) Assignee: ISP INVESTMENTS LLC, Wilmington, DE (US)

(*) Notice: Subject to any disclaimer, the term of this patent is extended or adjusted under 35 U.S.C. 154(b) by 789 days.

(21) Appl. No.: 16/615,001

(22) PCT Filed: Apr. 24, 2018

(86) PCT No.: PCT/US2018/029102
§ 371 (c)(1),
(2) Date: Nov. 19, 2019

(87) PCT Pub. No.: WO2018/212945
PCT Pub. Date: Nov. 22, 2018

(65) Prior Publication Data
US 2020/0079913 A1    Mar. 12, 2020

Related U.S. Application Data

(60) Provisional application No. 62/508,448, filed on May 19, 2017.

(51) Int. Cl.
*C08G 81/02* (2006.01)
*A61K 47/58* (2017.01)
(Continued)

(52) U.S. Cl.
CPC .......... *C08G 81/027* (2013.01); *A61K 31/135* (2013.01); *A61K 47/58* (2017.08);
(Continued)

(58) Field of Classification Search
CPC .. C08G 81/027; C08G 81/024; C08G 81/026; C08G 77/442; A61K 47/58; A61K 31/136; C04B 24/383; C08B 15/005; C08B 37/00; C08F 220/36; C08F 220/281; C08F 265/96; C08F 222/102; C08F 2800/20;
(Continued)

(56) References Cited

U.S. PATENT DOCUMENTS

| | | | | |
|---|---|---|---|---|
| 4,352,902 A * | 10/1982 | Nakayama | ............ | C08F 291/00 524/36 |
| 9,464,151 B2 * | 10/2016 | Hood | ............ | C08F 226/06 |
| 2016/0053131 A1 * | 2/2016 | Hood | ............ | C09D 143/04 523/456 |

OTHER PUBLICATIONS

Bandari et al. "Ring-Opening Metathesis Polymerization Based Pore-Size-Selective Functionalization of Glycidyl Methacrylate Based Monolithic Media: Access to Size-Stable Nanoparticles for Ligand-Free Metal Catalysis", Chemistry A European Journal, 2010, vol. 16, No. 15, p. 2, scheme 1. (Year: 2010).*

(Continued)

*Primary Examiner* — Michael M. Bernshteyn
(74) *Attorney, Agent, or Firm* — William J. Davis; Nathalie Tietcheu

(57) ABSTRACT

This application provides reactive, flexible, water-resistant hydroxyethylpyrrolidone methacrylate/glycidyl methacrylate copolymers having the structure:

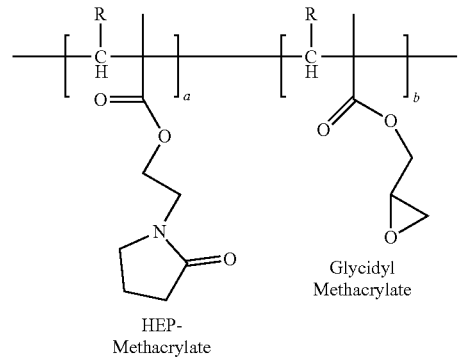

wherein a and b are integers, the sum of which less than 100, covalently linked to active agents that are useful in a wide variety of compositions. The present application also discloses hydroxyethylpyrrolidonemethacrylate/glycidyl methacrylate copolymer convently linked to one or more surface active moiety having a structure:

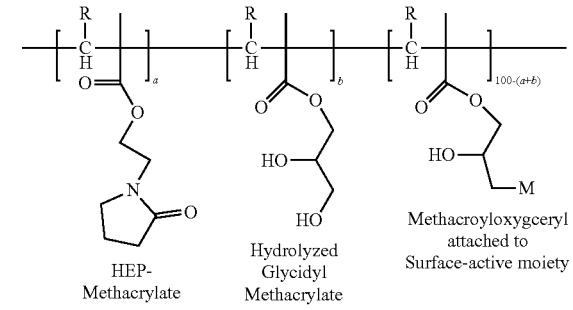

wherein a, b, and c are integers, the sum of which equals 100, and M is a surface-active moiety.

9 Claims, No Drawings

(51) Int. Cl.

| | |
|---|---|
| *A61K 31/135* | (2006.01) |
| *C04B 24/38* | (2006.01) |
| *C08B 15/00* | (2006.01) |
| *C08B 37/00* | (2006.01) |
| *C08F 220/36* | (2006.01) |
| *C08F 265/06* | (2006.01) |
| *C08G 77/442* | (2006.01) |
| *C09C 1/30* | (2006.01) |
| *C09D 11/101* | (2014.01) |
| *C09D 11/107* | (2014.01) |
| *D01F 1/10* | (2006.01) |
| *H01M 4/62* | (2006.01) |
| *C08F 220/28* | (2006.01) |
| *C08F 222/10* | (2006.01) |

(52) U.S. Cl.
CPC .......... *C04B 24/383* (2013.01); *C08B 15/005* (2013.01); *C08B 37/00* (2013.01); *C08F 220/281* (2020.02); *C08F 220/36* (2013.01); *C08F 222/102* (2020.02); *C08F 265/06* (2013.01); *C08G 77/442* (2013.01); *C08G 81/024* (2013.01); *C08G 81/025* (2013.01); *C09C 1/3072* (2013.01); *C09D 11/101* (2013.01); *C09D 11/107* (2013.01); *D01F 1/10* (2013.01); *H01M 4/622* (2013.01); *C08F 2800/20* (2013.01); *C08F 2810/20* (2013.01); *C08F 2810/50* (2013.01)

(58) Field of Classification Search
CPC . C08F 2810/20; C08F 2810/50; H01M 4/622; C09D 1/3072; C09D 11/101; C09D 11/107
See application file for complete search history.

(56) References Cited

OTHER PUBLICATIONS

Lin et al. "Preparation and characterization of covalent polymer functionalized graphene oxide", Journal of Mater. Chem., 2011, 21, pp. 3455-3461 (Year: 2011).*
Bandari et al. "Ring-Opening Metathesis Polymerization Based Pore-Size-Selective Functionalization of Glycidyl Methacrylate Based Monolithic Media: Access to Size-Stable Nanoparticles for Ligand-Free Metal Catalysis", Chemistry A European Journal, 2010, vol. 16, No. 15 (Year: 2010).*
Jani et al. "Dressing in Layers: Layering Surface Functionalities in Nanoporous Aluminum Oxide Membranes", Angew. Chem., Inter. Edition, 2010, vol. 49, pp. 7933-7937 (Year: 2010).*
Lin et al. Preparation and characterization of covalent polymer functionalized graphene oxide, Journal of Mater. Chem., 2011, 27, pp. 3455-3461. (Year: 2011).*
Jani, Amm et al. Dressing in Layers: Layering Surface Functionalities in Nanoporous Aluminum 16 Oxide Membranes. Angewandte Chemie International Edition, vol. 49, 2010, pp. 7933-7937; p. 7933, col. 1, paragraph 2; p. 7934, figure 1.
Lin, Yet al. Preparation and characterisation of covalent polymer functionalized graphene 16-17 i—Oxide. Journal of Materials Chemistry, vol. 21, 2011, pp. 3455-3461; abstract; p. 3456, figure 1; p. 3456, col. 1, paragraph 2.
Bandari et al. Ring-Opening Metathesis Polymerization Based Pore-Size-Selective 2,24—Functionalization of Glycidyl Methacrylate Based Monolithic Media: Access to Size-Stable Nanoparticles for Ligand-Free Metal Catalysis, Chemistry, A European Journal, vol. 16, No. 15, Apr. 19, 2010, pp. 4650-4658; p. 2, scheme 2.
International Search Report of PCT Application No. PCT/US2018/ 29102 filed on Apr. 24, 2018 and published on Nov. 22, 2018 under publication No. WO 2018/212945 A1 published on Nov. 22, 2018.

* cited by examiner

HYDROXYETHYLPYRROLIDONE ETHACRYLATE/GLYCIDYL ETHACRYLATE COPOLYMERS

FIELD OF THE INVENTION

The present application provides a composition of a copolymer of hydroxyethylpyrrolidone methacrylate/glycidyl methacrylate and one or more surface-active moiety and applications of the composition.

BACKGROUND OF THE INVENTION

The attachment of active agents to substrates using a variety of coating compositions is well known. A difficulty with the use of such compositions is that the active agents are leached from the substrates over time through a variety of means.

U.S. Pat. No. 2,882,262 discloses the production of polyhydroxyethylpyrrolidone acrylate or methacrylate, and their copolymers with acrylamide, styrene, methyl methacrylate, acrylonitrile, or dimethylaminoethyl methacrylate. These polymers were mixed with silver halide emulsions for photographic applications.

German Patent No. 2048312, discloses the production of copolymers based on polyhydroxyethyl (meth)acrylate with ethylene, butadiene, styrene, or simple C1-8 esters of (meth) acrylates formed in aromatic or aliphatic hydrocarbons, or (meth)alkylacrylamides, vinyl esters, or vinyl ethers, for moulded bodies, coatings, and adhesives.

WO 2011/063208 discloses the production of polymers made at 80-200° C. in alcohol or hydroalcoholic medium comprised of hydroxyethyl-pyrrolidone (meth)acrylate-based copolymers with either, 4-butylphenyl maleimide, octylacrylamide, triazoles, or vinyltrimethoxy-silane.

U.S. Pat. No. 5,362,830 discloses production of vinyl pyrrolidone/glycidyl (meth)acrylate copolymers in water, alcohol, or mixtures of both solvents to obtain crosslinked polymer gels.

US Publication Nos. US 2010/0190947 and 2012/0220741 discloses production of terpolymers or tetrapolymers of vinyl pyrrolidone, vinyl caprolactam, glycidyl methacrylate, with another polymerizable monomer.

US 2014/0296441 discloses terpolymers or tetrapolymers based on vinyl pyrrolidone and acetoacetate-based monomers.

US 2013/0150481 discloses a blend of hydroxyethylpyrrolidone (meth)acrylate with another monomer.

In view of the forgoing, there is a need for hydroxyethylpyrrolidone methacrylate and glycidyl methacrylate polymers. Also, such copolymers of hydroxyethylpyrrolidone methacrylate/glycidyl methacrylate and cross-linked copolymers of hydroxyethylpyrrolidone methacrylate/glycidyl methacrylate have advantages in various application including adhesives, aerosols, agricultural agents, anti-soil redeposition agents, batteries agents, beverages, biocides, cementing and construction agents, cleaning agents, coating agents, conductive materials, cosmetic agents, dental agents, decorated pigments, detergents, dispersants, drugs, electronics, encapsulations, foods, hair sprays, household-industrial institutional, inks and coatings, interlaminate adhesives, lithographic solutions, membrane additive agents, metal working fluids, oilfield agents, paints, paper, paper sizing agents, personal care agents, pharmaceuticals, pigment additives, plasters, plastic, printing, refractive index modifiers, sequestrants, soil release agents, static control agents and wood-care agents.

SUMMARY OF THE INVENTION

The primary objective of the present application is to provide a composition, comprised of a copolymer of hydroxyethylpyrrolidone methacrylate/glycidyl methacrylate having a structure:

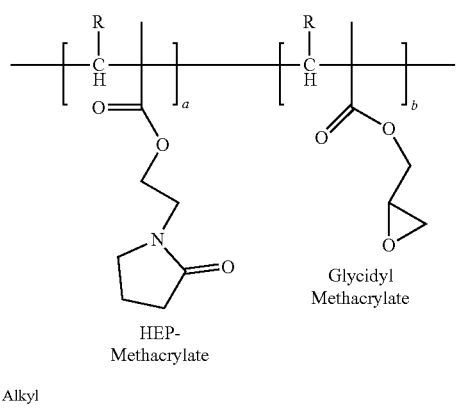

and one or more surface-active moiety; wherein a and b are numbers, mole %, the sum is less than 100; wherein the copolymer is covalently linked to the surface-active moiety.

Another aspect of present application is to provide a hydroxyethylpyrrolidone methacrylate/glycidyl methacrylate copolymer covalently linked to a surface-active moiety resulting in the structure:

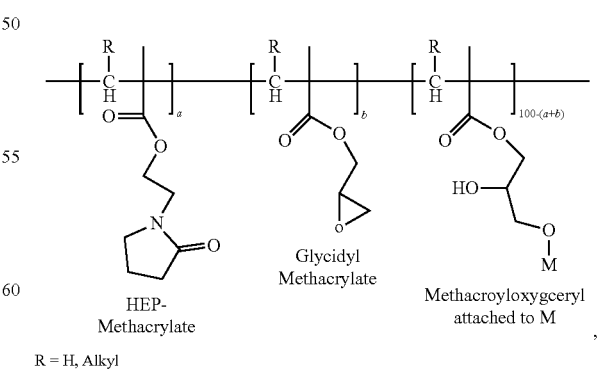

wherein a and b are numbers, mole %, the sum is less than 100; and M is the surface-active moiety.

Another objective of present application is to provide a cross-linked copolymer of hydroxyethylpyrrolidone methacrylate/glycidyl methacrylate having the structure:
(i)
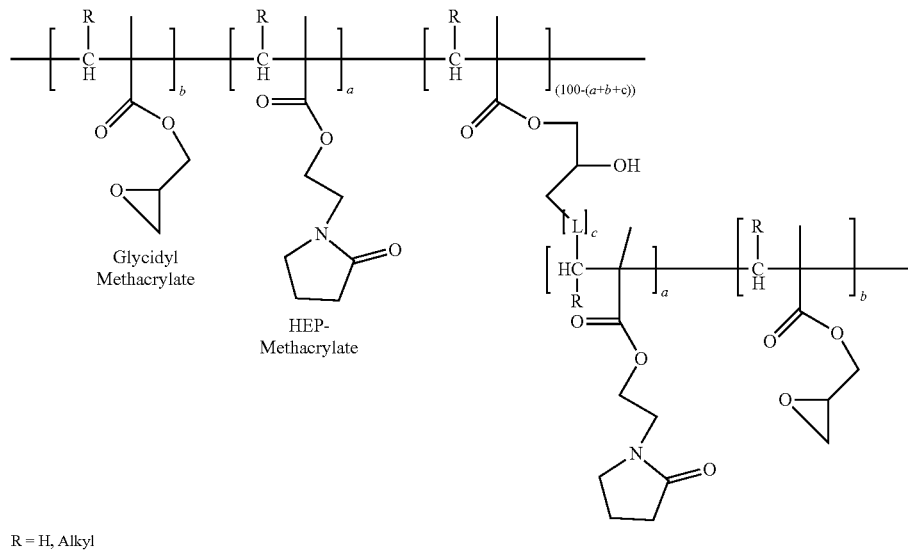
R = H, Alkyl
wherein a, b, c are numbers, mole %, the sum of which is less than 100 and L is difunctional moiety, or
(ii)
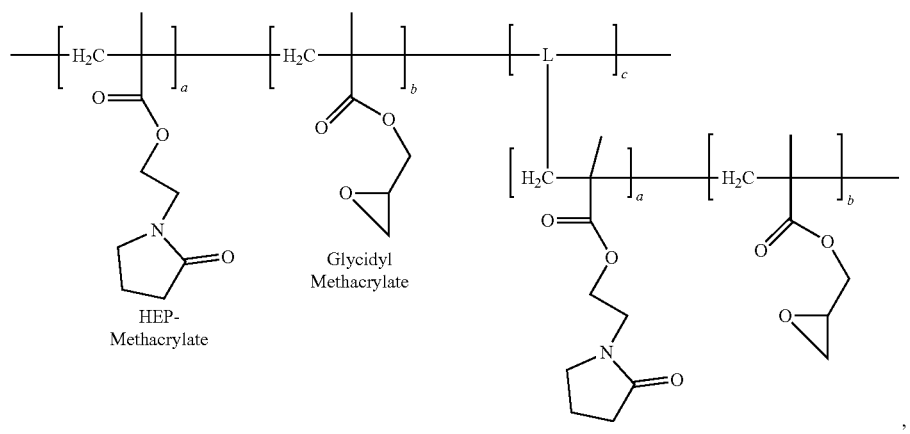

wherein a, b, c are numbers, mole %, the sum of which equals 100 and L is difunctional moiety.

Another objective of present application is to provide a cross-linked copolymer of hydroxyethylpyrrolidone methacrylate/glyceryl methacrylate covalently linked to a surface-active moiety resulting in the structure:

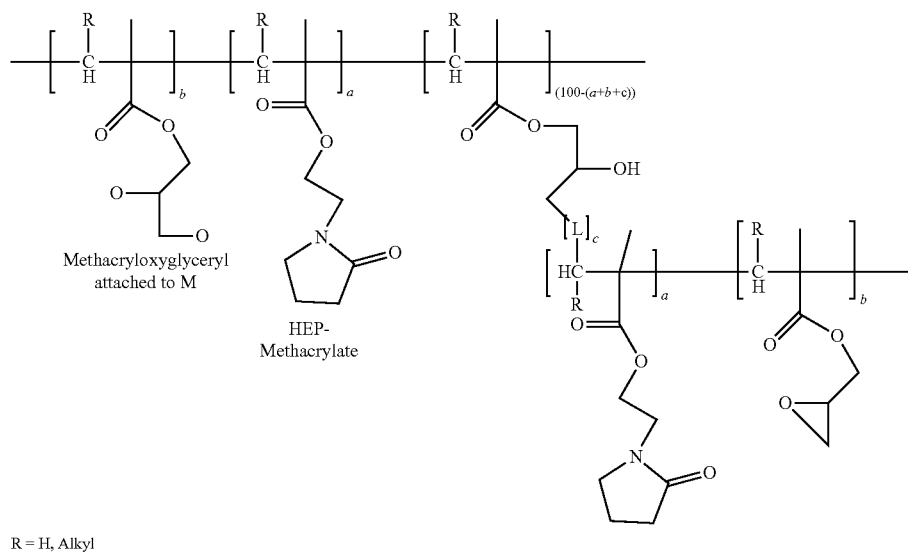

wherein a, b and c are numbers, mole %, the sum of which is less than 100, M is surface-active moiety, and L is difunctional moiety; or

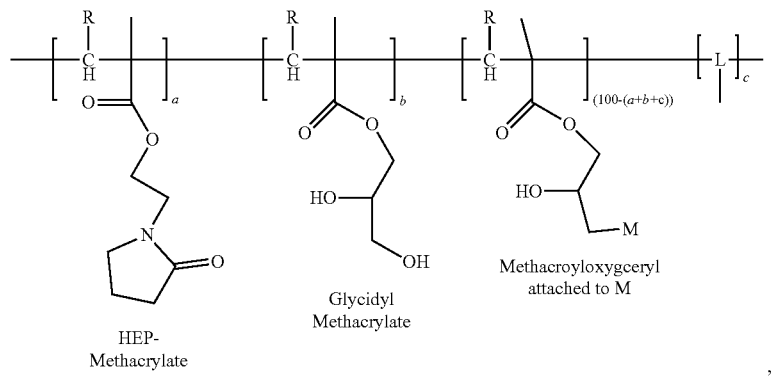

wherein a, b and c are numbers, mole %, the sum of which is less than 100, M is surface-active moiety, and L is difunctional moiety.

One more objective of the present application is to prepare a copolymer of hydroxyethylpyrrolidone methacrylate/glycidyl methacrylate by solution polymerization.

Another objective of the present application is to provide various applications of copolymers of hydroxyethylpyrrolidone methacrylate/glycidyl methacrylate and cross-linked copolymers of hydroxyethylpyrrolidone methacrylate/glycidyl methacrylate in adhesives, aerosols, agricultural agents, anti-soil redeposition agents, batteries agents, beverages, biocides, cementing and construction agents, cleaning agents, coating agents, conductive materials, cosmetic agents, dental agents, decorated pigments, detergents, dispersants, drugs, electronics, encapsulations, foods, hair sprays, household-industrial institutional, inks and coatings, interlaminate adhesives, lithographic solutions, membrane additive agents, metal working fluids, oilfield agents, paints, paper, paper sizing agents, personal care agents, pharmaceuticals, pigment additives, plasters, plastic, printing, refractive index modifiers, sequestrants, soil release agents, static control agents and wood-care agents.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included examples.

As used herein, the following terms, unless otherwise indicated, have the meanings set out below.

All percentages, ratio, and proportions used herein are based on a weight basis unless other specified.

The term "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or."

The term "at least one" refers to one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached.

The term "about" refers to a value that includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The term "comprising" (and any form of comprising, such as "comprise", "comprised", and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $B_{Xn}$, $B_{Xn+1}$, or combinations thereof" is intended to include at least one of: A, $B_{Xn}$, $B_{Xn+1}$, $ABx_{Xn}$, $AB_{Xn+1}$, $B_{Xn}B_{Xn+1}$, or $AB_{Xn}B_{Xn+1}$ and, if order is important in a particular context, also $B_{Xn}A$, $B_{Xn+1}A$, $B_{Xn+1}B_{Xn}$, $B_{Xn+1}B_{Xn}A$, $B_{Xn}B_{Xn+1}A$, $AB_{Xn+1}B_{Xn}$, $B_{Xn}AB_{Xn-1}$, or $B_{Xn+1}AB_{Xn}$. Continuing with this example, expressly included are combinations that contain repeats of one or more item or term, such as $B_{Xn}B_{Xn}$, AAA, $MB_{Xn}$, $B_{Xn}B_{Xn}B_{Xn+1}$, $AAAB_{Xn}B_{Xn+1}B_{Xn+1}B_{Xn+1}B_{Xn+1}$, $B_{Xn+1}B_{Xn}B_{Xn}AAA$, $B_{Xn+1}A$ $B_{Xn}AB_{Xn}B_{Xn}$, and so forth. The skilled artisan will understand that typically there is no limit on the number of items or terms in any combination, unless otherwise apparent from the context.

The term "each independently selected from the group consisting of" refers to a group appears more than once in a structure, that group can be selected independently each time it appears.

The term "acidic conditions" refers to conditions relating to the pH value of an aqueous solution. Pure water considered to be neutral, with a pH close to 7.0 at 25° C. Solutions with a pH value less than 7 considered to be acidic solutions.

The term "basic conditions" refers to conditions relating to the pH value. Pure water considered to be neutral, with a pH close to 7.0 at 25° C. Solutions with a pH value greater than 7 considered to be basic or alkaline.

The term "acryloyl" refers to a moiety having the generic structure:

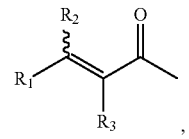

wherein each $R_1$, $R_2$, and $R_3$ is independently selected from the group consisting of hydrogen and functionalized and unfunctionalized alkyl, alkenyl, aryl, nitrile, formyl, carboxyl, carboxylate salt, carboxylic ester, carboxamide, halogen, thiocarboxylate, and combinations thereof.

The term "alkyl" refers to a functionalized or unfunctionalized monovalent straight-chain, branched-chain or cyclic $C_1$-$C_{60}$ group optionally having one or more heteroatoms. Particularly, an alkyl is a $C_1$-$C_{45}$ group and more particularly, a $C_1$-$C_{30}$ group. Particular, yet non-limiting examples of alkyl groups include methyl, ethyl, n-propyl, isopropyl, n-butyl, isobutyl, tert-butyl, cyclobutyl, n-pentyl, isopentyl, cyclopentyl, n-hexyl, cyclohexyl, n-heptyl, cycloheptyl, methylcyclohexyl, n-octyl, 2-ethylhexyl, tert-octyl, iso-norbornyl, n-dodecyl, tert-dodecyl, n-tetradecyl, n-hexadecyl, n-octadecyl, and n-eicosyl.

The term "alkyl (alk) acrylate" refers to an alkyl ester of an acrylic acid or an alkyl acrylic acid.

The term "alkyl (alk) acrylamide" refers to an alkyl amide of an acrylic acid or an alkyl acrylic acid.

The term "alkylene" refers to a functionalized or unfunctionalized divalent straight-chain, branched-chain or cyclic $C_1$-$C_{40}$ group optionally having one or more heteroatoms. Particularly, an alkylene is a $C_1$-$C_{45}$ group and more particularly, a $C_1$-$C_{30}$ group. Yet non-limiting examples of alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, —$CH_2$—$CH_2$—$CH_2$—$CH_2$—$CH_2$—$CH_2$—, —$CH_2$—$CH_2$—$CH_2$—$CH_2$—$CH_2$—$CH_2$—$CH_2$—, cyclopropylene, cyclobutylene, cyclopentylene, cyclohexylene, and the like.

The term "branched and unbranched alkyl groups" refers to alkyl groups, which can be straight chained or branched. For example, the alkyl groups have from 1 to about 60 carbon atoms, more particularly, from 1 to about 30 carbon atoms, and yet more particularly from 1 to about 6 carbon atoms. Branched groups include isopropyl, tert-butyl, and the like.

The term "hydrocarbyl" refers to a straight-chain and branched-chain alkyl, alkenyl, alkynyl, cycloalkyl, cycloalkenyl, aryl groups, and combinations thereof with optional heteroatom(s). A hydrocarbyl group can be mono-, di- or polyvalent.

The term "direct bond" refers to a C—C (single) bond. In another embodiment, the term "Direct bond" refers to a C=C (double) bond. "Direct bond" refers to a pair of electrons that hold together two adjacent atoms. Thus, when two atoms are separated by a direct bond, those two atoms are bonded together by a covalent bond. If a direct bond is attached to only one atom (X) and X is bonded to an adjacent atom (Y), then the direct bond represents a second bond between X and Y, i.e., the direct bond option provides a double bond between X and Y, at the expense of a hydrogen that would otherwise be bonded to Y. For example C—O—R where R is a direct bond denotes C=O.

The term "functionalized" refers to the state of a moiety that has one or more functional groups introduced to it by way of one or more functionalization reactions known to a person having ordinary skill in the art. Non-limiting examples of functionalization reactions include epoxidation, sulfonation, hydrolysis, amidation, esterification, hydroxylation, dihydroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. Particularly, functionalization of a moiety replaces one or more hydrogens in the moiety with one or more non-hydrogen groups, for e.g., alkyl, alkoxyl, cycloalkyl, alkenyl, cycloalkenyl, alkynyl, and/or aryl groups. Non-limiting examples of cycloalkyl groups include cyclopentane, cyclohexane, cycloheptane, and the like. Non-limiting examples of alkoxy groups include methoxy, ethoxy, n-propoxy, isopropoxy, and the like. Non-limiting examples of aryl groups include benzenes, naphthalenes (2 rings), anthracenes (3 rings), and the like.

The term "halogen" refers to chloro, bromo, iodo and fluoro, and in one embodiment is bromo and/or chloro.

The term "heteroatom" refers to atoms such as oxygen, nitrogen, sulfur, silicon, phosphorous, and/or halogen. The heteroatom(s) can be present as a part of one or more heteroatom-containing functional groups and/or as a part of one or more heterocyclic rings. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups.

The term "free radical addition polymerization initiator" refers to a compound used in a catalytic amount to initiate a free radical addition polymerization, and is used herein as simply "initiator". The term "free radical addition polymerization initiator" also refers to thermal and light activated initiators. The choice of "initiator" depends mainly upon its solubility and its decomposition temperature.

The term "monomer" refers to the repeat units comprising a polymer. The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units can range from very few, which more commonly can be called as oligomers, to very many. Non-limiting examples of polymers include homopolymers, and non-homopolymers such as copolymers, terpolymers, tetrapolymers and the higher analogues. The polymer can have a random, block, and/or alternating architecture.

The term "homopolymer" refers to a polymer that consists essentially of a single monomer type.

The term "non-homopolymer" refers to a polymer formed from two or more monomers and includes essentially all polymers that are not homopolymers. Nonlimiting examples of non-homopolymers include copolymers, terpolymers, tetramers, and the like, wherein the non-homopolymer is a random, blocked, or alternating polymer.

The term "copolymer" refers to chains comprising more than one type of monomer unit.

The term "terpolymer" refers to a non-homopolymer that comprises three different monomer types.

The terms "a", "b" and "c" refer to numbers commonly used in polymers and refers to mole % of each monomer, and in the present invention, a and b are numbers, the sum of which is less than 100.

The term "polymerization" refers to methods for chemically reacting monomer compounds to form polymer chains. The polymer chain can be alternating, branched, blocked, or random. The type of polymerization method can be selected from a wide variety of methods. Such methods include, but are not limited to, free radical polymerization methods, such as classical radical polymerization and controlled radical polymerization, Nitroxide Mediation Polymerization (NMP), Atom Transfer Radical Polymerization (ATRP), solution polymerization, and Reversible Addition Fragmentation Chain-Transfer (RAFT).

As used herein, "solution polymerization" refers to a polymerization process in which the polymer is dissolved in a liquid polymerization system, such as an inert solvent or monomer(s) or their blends. Solution polymerization comprises a homogeneous liquid polymerization system in the reactor. The temperature of a liquid polymerization system is below its supercritical or pseudo supercritical temperature, thus, solution polymerizations are performed below the supercritical temperature and/or pressure of the system. Conventional solution polymerization processes typically operate with more than 65 wt % inert solvent present in the polymerization system at pressures below 13 MPa (1885 psi) and temperatures between 40 and 160° C.

As used herein the term "solvent" refers to and includes, but is not limited to, ketones, such as acetone, methyl ethyl ketone, N-methyl pyrolidinone, dimethyl formamide, toluene, methanol, ethanol, hexane, tertiary butyl acetate and methyl acetate.

The term "non-aqueous" refers to a state of not being aqueous in nature. By "non-aqueous" it is generally meant that water is not deliberately added to the composition in any significant quantity. However, the term "non-aqueous" does not mean that small amounts of water cannot be present, for example as a consequence of its association with hygroscopic raw materials. Accordingly, for the purposes of this application, the term "non-aqueous" generally refers to that water is present in an amount no greater than about 5%, more preferably no greater than about 3% by weight based on the total weight of the composition.

The term "personal care composition" refers to such illustrative non-limiting compositions as skin, sun, oil, hair, and preservative compositions, including those to alter the color and appearance of the skin. The term personal care composition refers to compositions intended for use on or in the human body, such as skin, sun, oil, hair, cosmetic, and preservative compositions, including those to alter the color and appearance of the skin and hair. Potential personal care compositions include, but are not limited to, compositions for increased flexibility in styling, durable styling, increased humidity resistance for hair, skin, and color cosmetics, sun care water-proof/resistance, wear-resistance, and thermal protecting/enhancing compositions.

Polyvinyl lactams are non-toxic, ecologically friendly, water and organic soluble, film-forming stiff polymers (high Tg), which have excellent adhesion to a variety of substrates, such as metal, hair, skin, porcelain, plastics, polyesters, paper, concrete, and clays. The carbonyl group in Polyvinyl lactams has an ability to hydrogen bond/complex both high molecular weight entities such as polyphenols, tannins, polyacids and low molecular weight entities such as active pharmaceutical ingredients (as a drug excipient), inks or dye-mordants, and mycotoxins.

While the carbonyl oxygen atom in Polyvinyl lactams is a strong hydrogen bond acceptor, access to the oxygen atom is hindered due to the proximity of the oxygen atom in the polymeric backbone. Applicants have found that extending the Polyvinyl lactams group away from the polymeric backbone on a pendant group results in less steric hindrance and better access to the oxygen atom.

Polyvinyl lactams can be radical crosslinked by gamma-ray, x-ray, E-beam, UV-cured, and thermally activated by radical species to form an insoluble composite thereby rendering the PVP formulation as a hydrogel, or a surface treatment that is (semi)permanently affixed to the substrate on which it was coated. However, these crosslinking treatments require specialized equipment not readily available and the crosslinking conditions can damage other components in the formulation rendering them useless in the desired application.

The present application provides copolymers comprising vinyl lactams and vinyl glycidyl acrylates. The vinyl lactams, which have hydrogen bond/complex abilities, can comprise vinyl pyrrolidone, vinyl caprolactam, hydroxyalkyl-pyrrolidone-(meth)acrylates, hydroxyalkyl-pyrrolidone-(meth)acrylamides, and the like. The vinyl glycidyl acrylates, which contain a reactive epoxy-functionality, have an ability to covalently bond to a polymer. A preferred vinyl glycidyl acrylate is glycidyl methacrylate. By covalently bonding to the polymer, the polymeric water-soluble or water-dispersible complex will not be available to be washed away when exposed to aqueous solution.

The covalent (bond) linkage between the surface-active agent and the polymer is selected from a group consisting of an amino-hydroxy ester, a hydroxy ester ether, a thiohydroxy ester, an inorganic hydroxy ester, and a silicon-hydroxy ester, or combinations thereof.

The present application provides reactive, flexible, water-resistant hydroxyethylpyrrolidone methacrylate/glycidyl methacrylate copolymers. The copolymers can be used in a wide variety of compositions and applications.

Accordingly, the present application provides a surface modification composition, or delivery system, comprising the present copolymer. The present copolymer composition is reacted with useful actives and simultaneously or sequentially crosslinked onto a substrate under mild conditions. The present application also provides a means to decay the composition into a non-toxic glycerol entity, when not used or reacted with another agent so form environmental friendly and green compositional by product results.

Non-limiting examples of suitable polyvinyl lactams in the present application include:

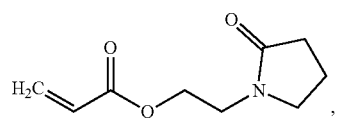
,

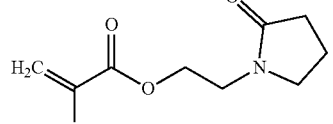
,

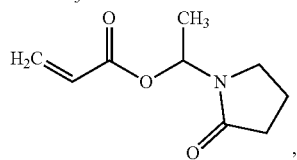
,

-continued

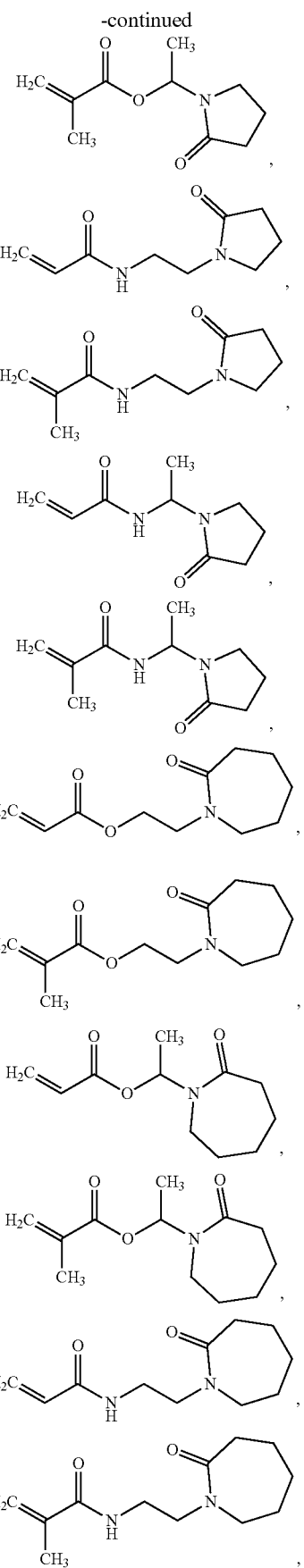

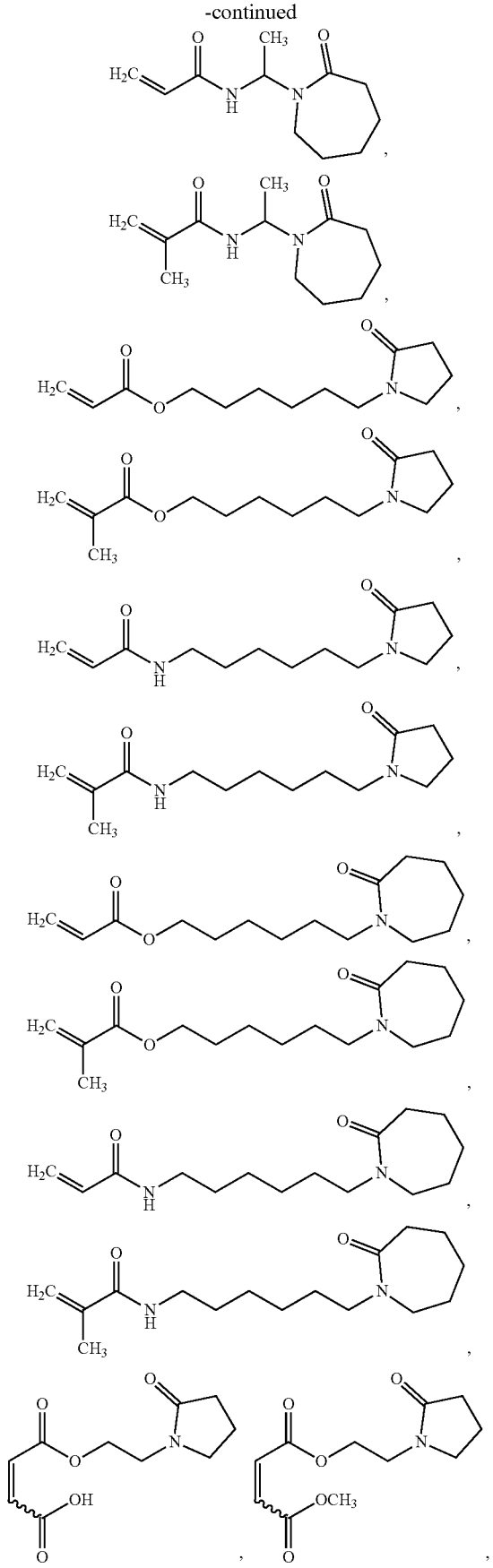

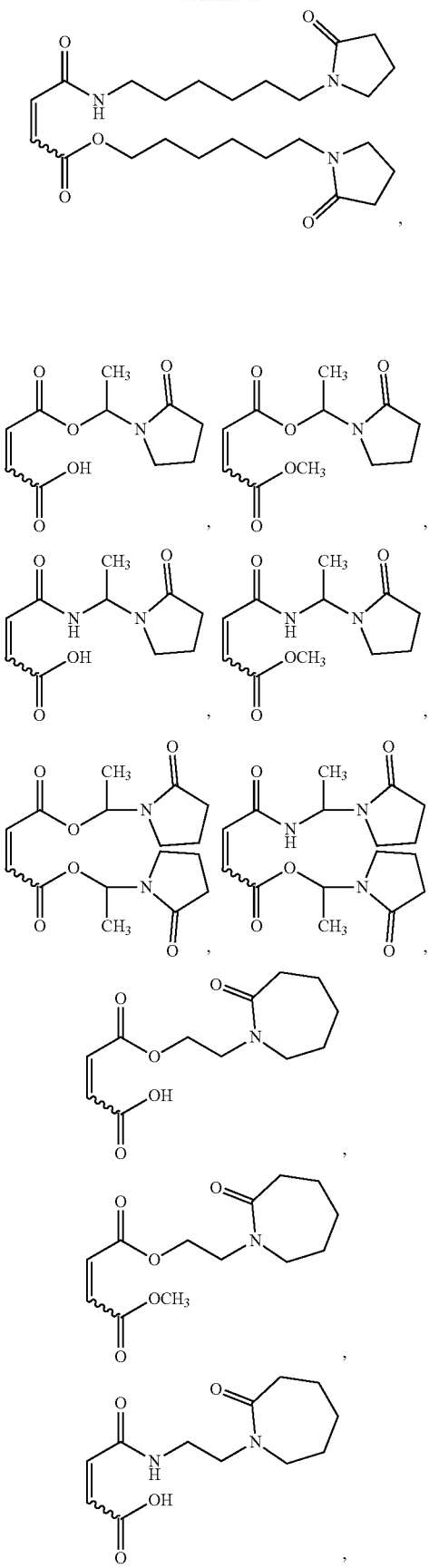
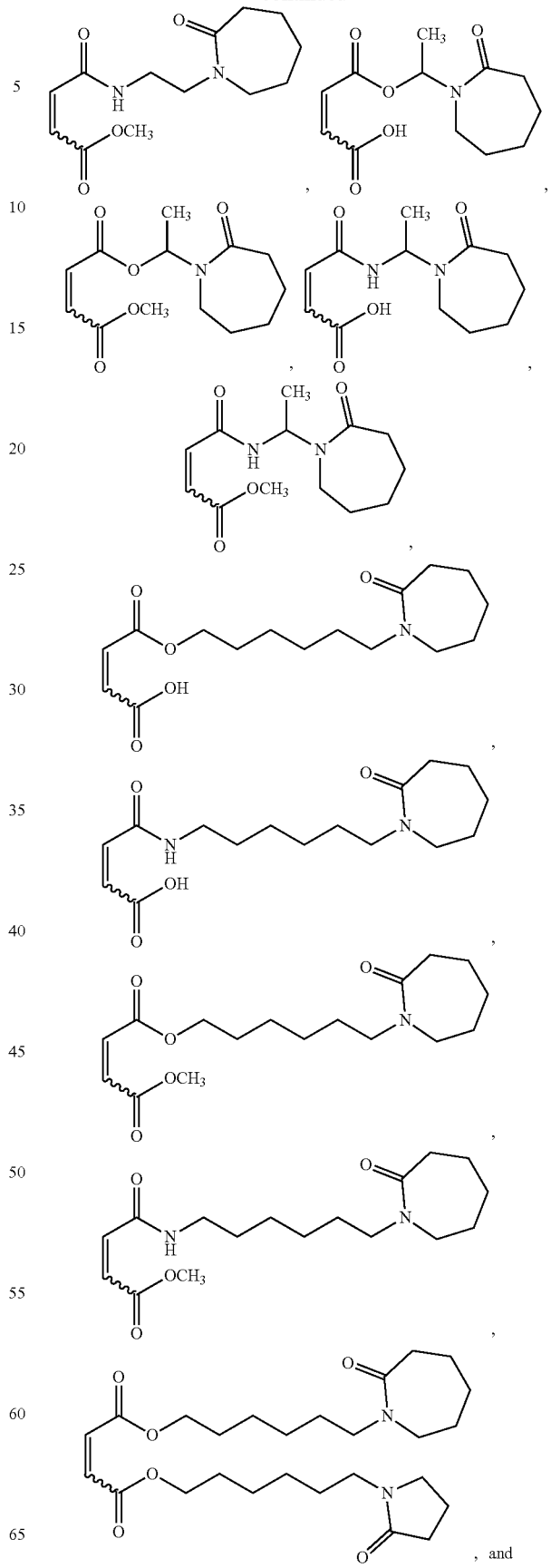

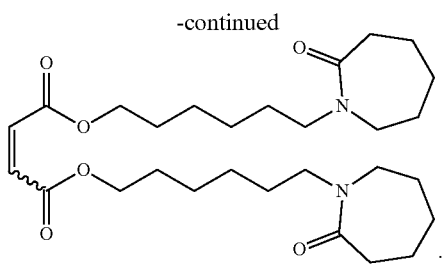

Other suitable examples that are relevant to the current application can be found in WO 2011/063208, the disclosure of which is incorporated herein by reference in its entirety.

Preferably, the polyvinyl lactam is hydroxyethylpyrrolidone methacrylate, set out below:

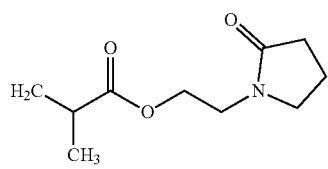

The present application provides reactive, flexible, water-resistant hydroxyethylpyrrolidone methacrylate/glycidyl methacrylate copolymers having the structure:

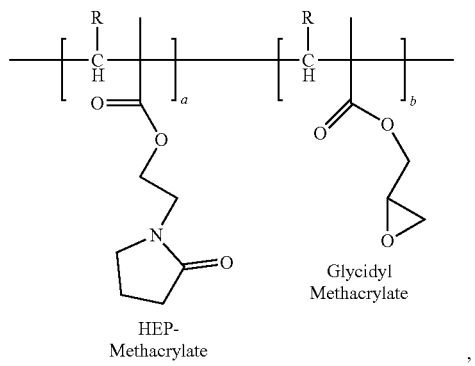

R = H, Alkyl wherein a and b are numbers, mole %, the sum is less than 100; wherein the copolymer is covalently linked to the surface-active moiety. In a preferred embodiment, each alkyl group independently contains from 1 to 6 carbon atoms.

In accordance with certain embodiments, a and b are numbers, mole %, ranging from about 5 to about 95. In accordance with another embodiment, a and b are numbers, mole %, ranging from about 10 to about 90. According to another embodiment, a and b are numbers, mole %, ranging from about 20 to about 80.

In accordance with certain embodiments, the sum of a and b is a number, mole %, ranging from about 40 to about 99.99. In accordance with another embodiment, the sum of a and b is a number, mole %, ranging from about 50 to about 80.

In accordance with certain embodiments, the surface-active moiety is selected from the group consisting of organic, modified inorganic, and modified allotrope moiety.

In accordance with certain embodiments, the organic moiety is selected from the group consisting of natural, semisynthetic and synthetic moiety.

In accordance with certain embodiments, the natural moiety is selected from the group consisting of polysaccharide, modified polysaccharide, biofunctional peptide, protein, glycol-protein, lipo-protein, polypeptide, DNA, RNA, and a pharmaceutical active.

In accordance with certain embodiments, the polysaccharide moiety is selected from the group consisting of starch, galactomannan, agar, pectin, natural gum, polydextrose, xanthan gum, carboxymethyl cellulose, hydroxyethyl cellulose, hydroxypropyl cellulose and modified cellulose.

In accordance with certain embodiments, the semisynthetic moiety is one or more synthetic polymer grafted on a polysaccharide.

In accordance with certain embodiments, the synthetic polymer, grafted on a polysaccharide, is prepared from at least one vinyl monomer selected from a group consisting of meth(acrylates), alkyl meth(acrylates), meth(acrylic acid), maleic anhydride, N-vinyl lactams, N-vinyl-2-pyrrolidone, N-vinylcaprolactam, styrene, acrylamide, alkyl acrylamides, 2-hydroxyethyl methacrylate and vinyl acetate.

In accordance with certain embodiments, the synthetic moiety is selected from the group consisting of maleic anhydride-copolymer, itaconic anhydride copolymer, maleic acid-copolymer, itaconic acid-copolymer, polyterphtalate, polyalkyd, polyester, polyurethane, polyether, epoxy, nylon, poly(meth)acrylate, polyolefin, polyvinyl ether, polystyrene, poly-vinyl-substituted-monomer, poly(meth)acrylamide, polyethyleneglycol, polypropyleneglycol, polysiloxane, polydimethylsiloxane, silicone polymer, polysulfone, polyamide, polylactam, a pharmaceutical active, a sunscreen active, polyvinylacetate, polyvinyl alcohol, polyvinylpyrrolidone, polyvinylcaprolactam, vinylpyrrolidone copolymers, vinylcaprolactam copolymers, polyvinylformamide, polyvinyl imidazole, polyvinyl acetamide and polyvinyl chloride.

In accordance with certain embodiments, the modified inorganic moiety is selected from the group consisting of modified gypsum, modified silica, modified pigments, modified calcium carbonate, modified aluminum oxide, modified titanium dioxide, modified inorganic nanotubes, modified silicates and modified clays. In accordance with another embodiment, the modified inorganic moiety comprises a reactive functionality selected from the group consisting of —COOH, —OH, amine, acid amides, nitrile, thiol, epoxy, oxetane, aziridine, isocyante, oxazoline, benzoxazine and combinations thereof.

In accordance with certain embodiments, the modified allotrope moiety is selected from the group consisting of modified graphene, modified fullerenes, modified carbon nanotube, modified graphite, and modified carbon black. In accordance with another embodiment, the modified allotrope moiety comprises a reactive functionality selected from the group consisting of —COOH, —OH, amine, acid amides, nitrile, thiol, epoxy, oxetane, aziridine, isocyante, oxazoline, benzoxazine and combinations thereof.

In accordance with certain embodiments, the surface-active moiety comprises a reactive functionality selected from the group consisting of —COOH, —OH, amine, amide acid amides, imide, aldehydic, carbanion, thiol, epoxy, oxetane, aziridine, isocyante, oxazoline, phosphoric, sulfuric, sulfonic, boric, oxazine and combinations thereof.

In accordance with certain embodiments, carbon nanotubes modified with hydroxyl (—OH) group can be found in Young-Sun et al (Carbon Letters, vol. 11, No. 4 pp. 311-315).

In accordance with certain embodiments, the —COOH group comprising moieties include but are not limited to monofunctional, difunctional and polyfunctional carboxylic acids. Non-limiting examples are acrylic acid, methacrylic acid, itaconic acid, maleic acid, fumaric acid, oleic acid, crotonic acid, isocrotonic acid, cinnamic acid, allylacetic acid, 2-pentenoic acid, 3-methyl-2-hexenoic acid, 2-hexenoic acid, 2-heptenoic acid, 4-ethyl-2-octenoic acid, 2-nonenoic acid, 9-decylenic acid, stillingic acid, 10-undecenoic acid, 9-dodecylenic acid, palmitoleic acid, oleic acid, ricinoleic acid, petroselenic acid, vaccenic acid, linoleic acid, linolenic acid, eleostearic acid, licanic acid, parinaric acid, gadoleic acid, arachidonic acid, cetoleic acid, erucic acid, nervonic acid, and the like.

In accordance with certain embodiments, —OH group comprising moieties include but are not limited to, monofunctional, difunctional and polyfunctional hydroxy group containing compounds. Non-limiting examples are hydroxyl-containing polymers include poly(vinyl alcohol), partially hydrolyzed poly(vinyl acetate/vinyl alcohol) or copolymers containing hydroxyethyl(meth)acrylate, copolymers containing hydroxypropyl(meth)acrylate, including modified and unmodified poly(vinyl alcohol), such as, acetoacetylated, anionic PVA, carboxylated PVA, non-cationic modified PVA and sulfonated. Copolymers of PVA, for example with ethylene oxide or propylene oxide, are also envisioned. Non-limiting examples are phenoxy or poly (hydroxy ethers) materials include compositions derived from dihydric mononuclear phenols such as alkenylcatechols and halogenated catechols, alkenylhydroquinones and halogenated hydroquinones, alkenylresorcinols and halogenated resorcinols, catechol, hydroquinone, substituted hydroquinones such as alkylhydroquinones, substituted resorcinols (e.g., 5-methylresorcinol, 2,5-dimethylresorcinol, 5-ethylresorcinol, 4,5-dimethylresorcinol), resorcinol and substituted catechols. Examples of bis(4-hydroxyphenyl)alkanes such as bis(4-hydroxyphenyl)methane, dihydric polynuclear phenol include bisphenol A, 1,1-bis(4-hydroxyphenyl)ethane and 2,2-bis(4-hydroxyphenyl)butane, bis(4-hydroxyphenyl)cycloalkanes such as 1,1-bis(4-hydroxyphenyl)cyclohexane and compounds such as 4,4'-dihydroxybiphenyl.

In accordance with another embodiment, amine group comprising moieties include but are not limited to monofunctional, difunctional and polyfunctional amine group containing compounds.

Particularly, non-limiting examples of compounds having at least two amino groups include 1,2-ethanediamine, 1,2-propanediamine, 1,3-propanediamine, 1,2-butanediamine, 1,3-butanediamine, 2,3-butanediamine, 1,4-butanediamine, but-2-ene-1,4-diamine, 1,2-pentanediamine, 1,5-pentanediamine, 1,2-hexanediamine, 1,6-hexanediamine, 1,10-decanediamine, 1,2-dodecanediamine, 1,12-dodecanediamine, 3-methylpentane-1,5-diamine, 2,5-dimethyl-1,3-hexanediamine, 2,2,4-trimethyl-1,3-pentanediamine, 1,2-cyclohexanediamine, 1,4-cyclohexanediamine, 1,4-bis(aminomethyl)cyclohexane, 2,2-bis(4-aminophenyl)propane, 2,2-bis [4-(2-aminopropyl)phenyl]propane, diethylene triamine, triethylene tetramine, tetraethylene pentamine, pentaethylene hexamine, piperazine, isophoronediamine, polyethyleneimines, and the like.

Non-limiting examples of suitable polymers include polyamines, polyaminoamides, and quaternary polyammonium classes of polymers, such as:
  a. homopolymers and copolymers derived from acrylic or methacrylic esters or amides. The copolymers can contain one or more units derived from acrylamides, methacrylamides, diacetone acrylamides, acrylic or methacrylic acids or their esters, vinyllactams such as vinyl pyrrolidone or vinyl caprolactam, and vinyl esters. Non-limiting, specific examples include: copolymers of acrylamide and dimethyl amino ethyl methacrylate quaternized with dimethyl sulfate or with an alkyl halide; copolymers of acrylamide and methacryloyl oxyethyl trimethyl ammonium chloride; the copolymer of acrylamide and methacryloyl oxyethyl trimethyl ammonium methosulfate; copolymers of vinyl pyrrolidone and dialkylaminoalkyl acrylate or methacrylate, optionally quaternized, such as the products sold under the name Gafquat™ by Ashland Specialty Ingredients; terpolymers of dimethyl amino ethyl methacrylate, vinyl caprolactam, and vinyl pyrrolidone such as the product sold under the name Gaffix™ VC 713 by Ashland Specialty Ingredients; the vinyl pyrrolidone/methacrylamidopropyl dimethylamine copolymer, marketed under the name Styleze™ CC 10 by Ashland Specialty Ingredients; and the vinyl pyrrolidone/quaternized dimethyl amino propyl methacrylamide copolymers such as the product sold under the name Gafquat™ HS 100 by Ashland Specialty Ingredients (Wayne, NJ).
  b. derivatives of cellulose ethers containing quaternary ammonium groups, such as hydroxy ethyl cellulose quaternary ammonium that has reacted with an epoxide substituted by a trimethyl ammonium group.
  c. derivatives of cationic cellulose such as cellulose copolymers or derivatives of cellulose grafted with a hydrosoluble quaternary ammonium monomer, as described in U.S. Pat. No. 4,131,576, such as hydroxy alkyl cellulose, and hydroxymethyl-, hydroxyethyl- or hydroxypropyl-cellulose grafted with a salt of methacryloyl ethyl trimethyl ammonium, methacrylamidopropyl trimethyl ammonium, or dimethyl diallyl ammonium.
  d. cationic polysaccharides such as described in U.S. Pat. Nos. 3,589,578 and 4,031,307, guar gums containing cationic trialkyl ammonium groups, and guar gums modified by a salt, e.g., chloride of 2,3-epoxy propyl trimethyl ammonium.
  e. polymers composed of piperazinyl units and alkylene or hydroxy alkylene divalent radicals with straight or branched chains, possibly interrupted by atoms of oxygen, sulfur, nitrogen, or by aromatic or heterocyclic cycles, as well as the products of the oxidation and/or quaternization of such polymers.
  f. water-soluble polyamino amides prepared by polycondensation of an acid compound with a polyamine. These polyamino amides can be reticulated.
  g. derivatives of polyamino amides resulting from the condensation of polyalkylene polyamines with polycarboxylic acids followed by alkylation by bi-functional agents.
  h. polymers obtained by reaction of a polyalkylene polyamine containing two primary amine groups and at least one secondary amine group with a dioxycarboxylic acid chosen from among diglycolic acid and saturated dicarboxylic aliphatic acids having 3 to 8 atoms of carbon. Such polymers include those described in U.S. Pat. Nos. 3,227,615 and 2,961,347.
  i. cyclopolymers of alkyl diallyl amine or dialkyl diallyl ammonium such as the homopolymer of dimethyl diallyl ammonium chloride and copolymers of diallyl dimethyl ammonium chloride and acrylamide.
  j. quaternary diammonium polymers such as hexadimethrine chloride.

k. quaternary polyammonium polymers, including, for example, Mirapol® A 15, Mirapol® AD1, Mirapol® AZ1, and Mirapol® 175 products sold by Miranol.
l. quaternary polymers of vinyl pyrrolidone and vinyl imidazole such as the products sold under the names Luviquat® FC 905, FC 550, and FC 370 by BASF Corporation.
m. quaternary polyamines, and/or
n. reticulated polymers known in the art.

Other non-limiting examples of amine group containing polymers that can be used include cationic proteins, non-cationic or hydrolyzed cationic proteins, polyalkyleneimines such as polyethyleneimines, polymers containing vinyl pyridine or vinyl pyridinium units, condensates of polyamines and epichlorhydrins, quaternary polyurethanes, and derivatives of chitin. The non-limiting examples can comprise a fatty amine Non-limiting examples of suitable fatty amines include: dodecyl amines, cetyl amines, stearyl amines such as stearamidopropyl dimethylamine, and blends thereof.

In accordance with certain embodiments, acid amides group comprising moieties include but are not limited to monofunctional, difunctional and polyfunctional acid amides group containing compounds.

Non-limiting examples of fumaric acid monoamides include but are not limited to N-methyl fumaric acid amide, N-ethyl fumaric acid amide, N-n-propyl fumaric acid amide, N-allyl fumaric acid amide, N-n-butyl fumaric acid amide, N-tertiary butyl fumaric acid amide, N-n-hexyl fumaric acid amide, N-(2-ethylhexyl) fumaric acid amide, N-n-heptyl fumaric acid amide, N-n-nonyl fumaric acid amide, N-n-dodecyl fumaric acid amide, N-n-decosyl fumaric acid amide, N-cyclohexyl fumaric acid amide, N-(2-bromoethyl) fumaric acid amide, N-(2-fluoroethyl) fumaric acid amide, N-(2-chlorohexyl) fumaric acid amide, N-methoxymethyl fumaric acid amide, N-n-tetradecyl fumaric acid amide, N-n-hexadecyl fumaric acid amide, N-n-octadecyl fumaric acid amide, N-benzyl fumaric acid amide, N-(2-phenyl-ethyl) fumaric acid amide, N-(beta-phenylpropyl) fumaric acid amide, N-(4-phenyl-n-butyl) fumaric acid amide, N-phenyl fumaric acid amide, N-naphthyl fumaric acid amide, N-(ortho-chlorophenyl) fumaric acid amide, N-(meta-bromophenyl) fumaric acid amide, N-(p-flurophenyl) fumaric acid amide, N-(ortho-iodophenyl) fumaric acid amide, N-(ortho-methoxyphenyl) fumaric acid amide, N-(meta-methoxyphenyl) fumaric acid amide, N-(para-ethoxyphenyl) fumaric acid amide, N-(para-n-butoxyphenyl) fumaric acid amide, N-(para-chloro-meta-methylphenyl) fumaric acid amide, N-(ortho-methylphenyl) fumaric acid amide, N-(meta-methylphenyl) fumaric acid amide, N-(ortho-ethylphenyl) fumaric acid amide, N-(meta-ethylphenyl) fumaric acid amide, N-(para-ethylphenyl) fumaric acid amide, N-para-tolyl fumaric acid amide, N-(4-hydroxy-naphthyl) fumaric acid amide, N,N-dimethyl fumaric acid amide; N,N-diethyl fumaric acid amide; N,N-di-n-butyl fumaric acid amide; N-methyl-N-ethyl fumaric acid amide; N,N-di-isobutyl fumaric acid amide; N,N-di-sec-butyl fumaric acid amide; N,N-di-tertiarybutyl fumaric acid amide; N,N-diamyl fumaric acid amide; N,N-di-n-hexyl fumaric acid amide; N,N-di-n-heptyl fumaric acid amide; N,N-di-n-octyl fumaric acid amide; N,N-di-n-2-ethylhexyl fumaric acid amide; N,N-di-isooctyl fumaric acid amide; N,N-di-n-nonyl fumaric acid amide; N,N-di-n-decyl fumaric acid amide; N,N-di-n-undecyl fumaric acid amide; N,N-di-n-dodecyl fumaric acid amide; N,N-di-n-tridecyl fumaric acid amide; N,N-di-n-tetradecyl fumaric acid amide; N,N-di-n-pentadecyl fumaric acid amide; N,N-di-n-hexadecyl fumaric acid amide; N,N-di-n-heptadecyl fumaric acid amide; N,N-di-n-octadecyl fumaric acid amide; N-methyl-N-(2-bromoethyl) fumaric acid amide; N-methyl-N-n-propyl fumaric acid amide; N-methyl-N-isopropyl fumaric acid amide; N-methyl-N-n-butyl fumaric acid amide; N-methyl-N-isobutyl fumaric acid amide; N-methyl-N-sec-butyl fumaric acid amide; N-methyl-N-tertiary butyl fumaric acid amide; N-methyl-N-amyl fumaric acid amide; N-methyl-N-n-pentyl fumaric acid amide; N-methyl-N-n-hexyl fumaric acid amide; N-methyl-N-n-heptyl fumaric acid amide; N-methyl-N-n-octyl fumaric acid amide; N-methyl-N-isooctyl fumaric acid amide; N-methyl-N-2-ethylhexyl fumaric acid amide; N-methyl-N-n-nonyl fumaric acid amide; N-methyl-N-n-decyl fumaric acid amide; N-methyl-N-n-undecyl fumaric acid amide; N-methyl-N-n-dodecyl fumaric acid amide; N-methyl-N-n-tridecyl fumaric acid amide; N-methyl-N-n-tetradecyl fumaric acid amide; N-methyl-N-n-pentadecyl fumaric acid amide; N-methyl-N-n-hexadecyl fumaric acid amide; N-methyl-N-n-heptadecyl fumaric acid amide; N-methyl-N-n-octadecyl fumaric acid amide; N,N-dibenzyl fumaric acid amide; N,N-diphenyl fumaric acid amide; N,N-diphenethyl fumaric acid amide; N-methyl-N-benzyl fumaric acid amide; N-methyl-N-phenyl fumaric acid amide; N-tertiary butyl-N-benzyl fumaric acid amide; N,N-dicyclohexyl fumaric acid amide, and the like. The carboxylic acid group in fumaric acid monoamide can be free or converted into a salt of a metal ion, ammonium ion, or an organic amino cation.

In accordance with certain embodiments, the surface-active moiety comprises functionalized or non-functionalized compounds having a reactive functionality selected from the group consisting of —COOH, —OH, amine, acid amides, nitrile, thiol, epoxy, oxetane, aziridine, isocyante, oxazoline, benzoxazine and combinations thereof.

In accordance with certain embodiments, the present application also discloses compositions, comprised of: a copolymer of hydroxyethylpyrrolidone methacrylate/glycidyl methacrylate having a structure:

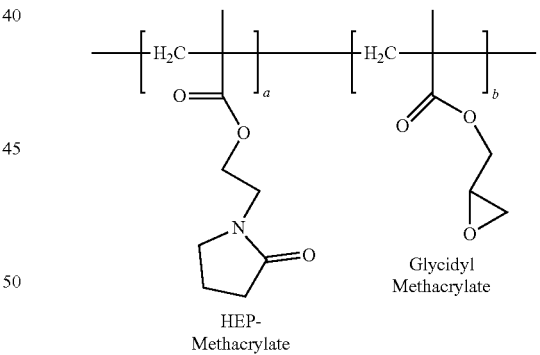

and
one or more surface-active moiety; wherein a and b are numbers, mole %, the sum is less than 100; wherein the copolymer is covalently linked to the surface-active moiety; and wherein the surface-active moiety is selected from a group consisting of carboxymethyl cellulose, hydroxyethyl cellulose, hydroxypropyl cellulose and/or hydrophobically modified hydroxypropyl cellulose-stearate.

In accordance with certain embodiments, the present application discloses compositions comprising: I) (i) about 0.1 wt. % to about 30 wt. % of a surface-active moiety and a copolymer of hydroxyethylpyrrolidone methacrylate/glycidyl methacrylate having the structure:

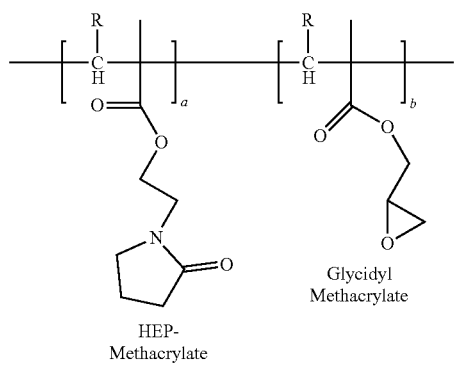

HEP-Methacrylate

Glycidyl Methacrylate

R = H, Alkyl

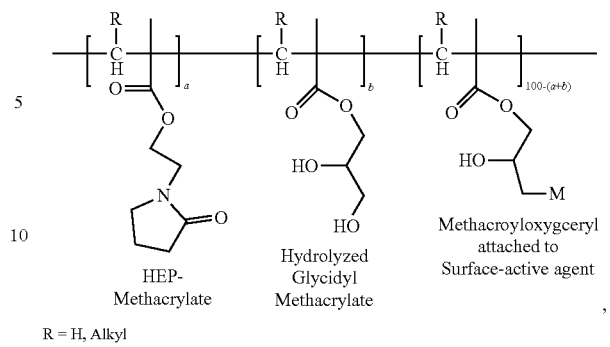

HEP-Methacrylate

Hydrolyzed Glycidyl Methacrylate

Methacroyloxygceryl attached to Surface-active agent

R = H, Alkyl wherein a and b are mole %, the sum is less than 100; and wherein the copolymer is covalently linked to the surface-active moiety, or ii) about 0.1 wt. % to about 30 wt. % of a hydroxyethylpyrrolidone methacrylate/glycidyl methacrylate copolymer covalently linked to surface-active moiety resulting in the structure:

wherein a and b are numbers, mole %, the sum is less than 100; M is the surface-active moiety, and (II) about 1 wt. % to 99 wt. % of at least one additive.

In accordance with certain embodiments, the present application discloses a cross-linked copolymer of hydroxyethylpyrrolidone methacrylate/glycidyl methacrylate having the structure:

(i)

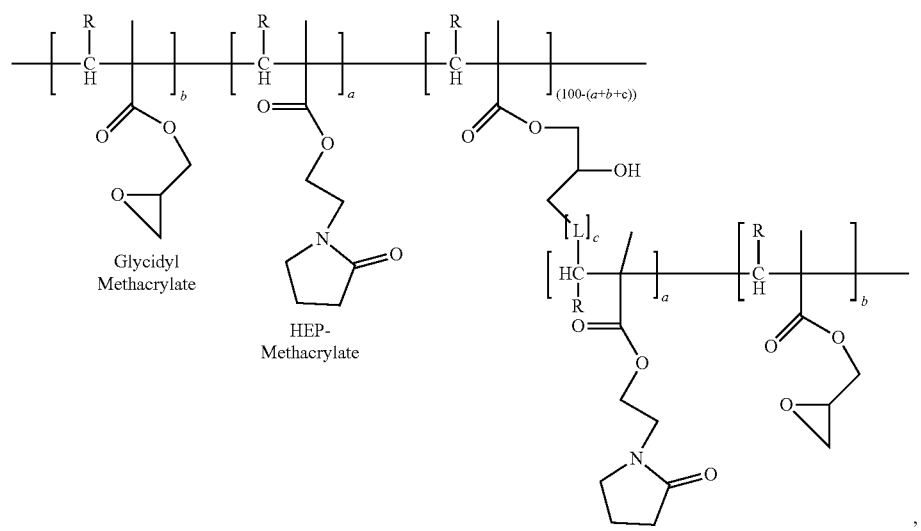

Glycidyl Methacrylate

HEP-Methacrylate

R = H, Alkyl wherein a, b, c are numbers, mole %, the sum of which is less than 100 and L is difunctional moiety; or (ii)

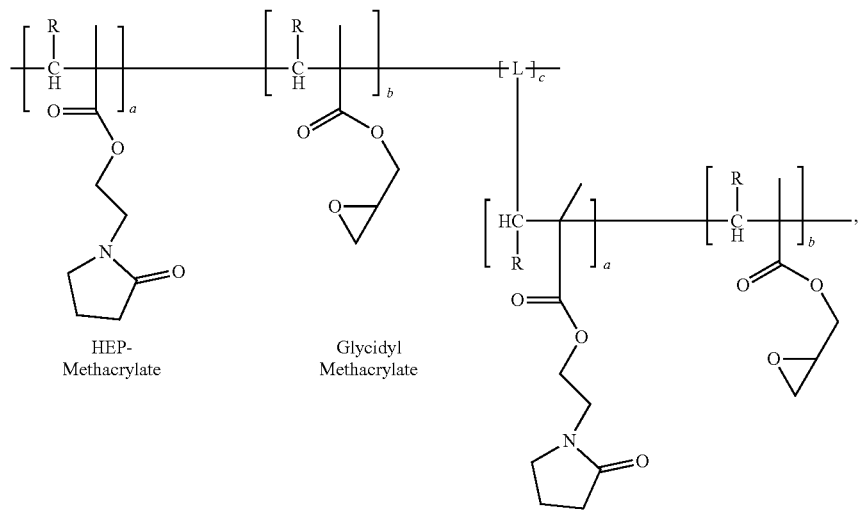

R = H, Aklyl wherein a, b, c are numbers, mole %, the sum of which equals 100 and L is difunctional moiety.

In accordance with certain embodiments, c is a number, mole %, ranging from about 0.01 to about 40.

In accordance with certain embodiments, the present application discloses a cross-linked copolymer of hydroxyethylpyrrolidone methacrylate/glyceryl methacrylate covalently linked to one or more surface-active moiety resulting in the structure:

(i)

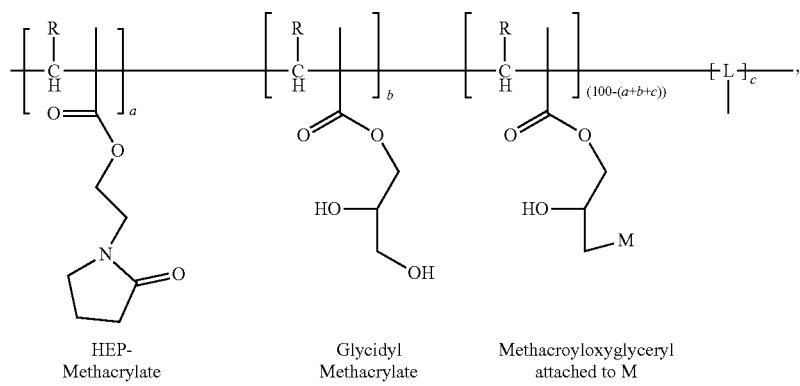

R = H, Alkyl wherein a, b and c are numbers, mole %, the sum of which is less than 100, M is surface-active moiety and L is difunctional moiety; or (ii)

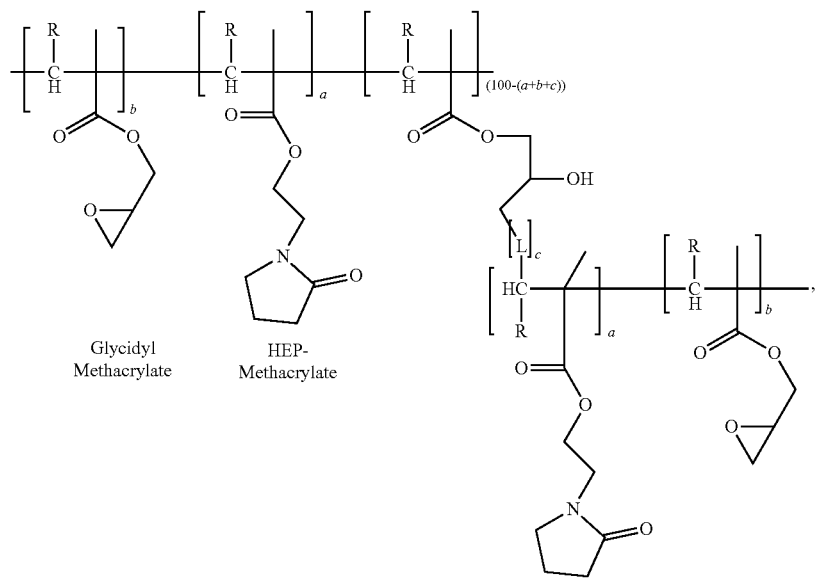

Glycidyl Methacrylate    HEP-Methacrylate

R = H, Aklyl wherein a, b and c are numbers, mole %, the sum of which is less than 100, M is surface-active moiety, L is difunctional moiety.

In accordance with certain embodiments, the difunctional moiety is selected from the group consisting of methylene bis-acrylamide, divinylbenzene, divinyl sulfone, divinylimidazole, divinylimidiazolidone, polyethyleneglycol diacrylate, polyethyleneglycol dimethacrylate, polypropyleneglycol diacrylate, polypropyleneglycol dimethacrylate, divinyltetramethyl disiloxane, divinyl phenylphosphine, divinyl formamide, pentaerythritol diacrylate, pentaerythritol triacrylate, pentaerythritol dimethacrylate, pentaerythritol trimethacrylate, pentaerythritol triallyl ether, cyclohexyldimethanol diacrylate, cyclohexyldimethanol dimethacrylate, butadiene, pentadiene, hexadiene, heptadiene octadiene, 1,9 decadiene, bis-alcohol, a triol, bis-diol, pentol, bis-triol, a triose, a tetrose, a pentose, a hexose, a uronic acid, gluonic acid, glucouronic acid, an aldose, a ketose, an amino-alcohol, ethoxylated amino-alcohol, bis-amine, tris-amine, diethylene tetra-amine, and ethoxylated bis-amino of carbon chain-length $C_2$-$C_{30}$.

In accordance with one embodiment, the present application discloses a composition comprising:

i) about 0.1 wt. % to about 30 wt. % of a cross-linked copolymer of hydroxyethylpyrrolidone methacrylate/glyceryl methacrylate having a structure:

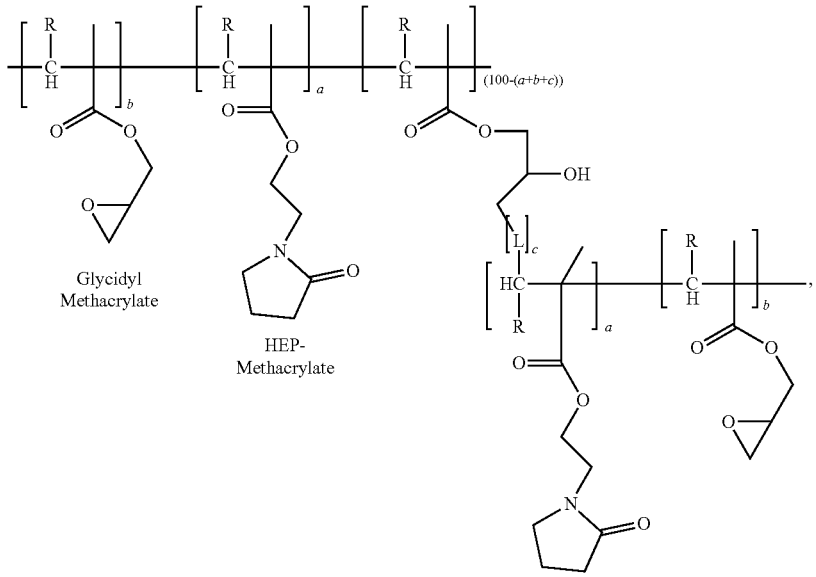

Glycidyl Methacrylate    HEP-Methacrylate

R = H, Aklyl wherein a, b, c are numbers, mole %, the sum of which is less than 100 and L is difunctional moiety; or (ii) about 0.1 wt. % to about 30 wt. % of a cross-linked copolymer of hydroxyethylpyrrolidone methacrylate/glyceryl methacrylate having the structure:

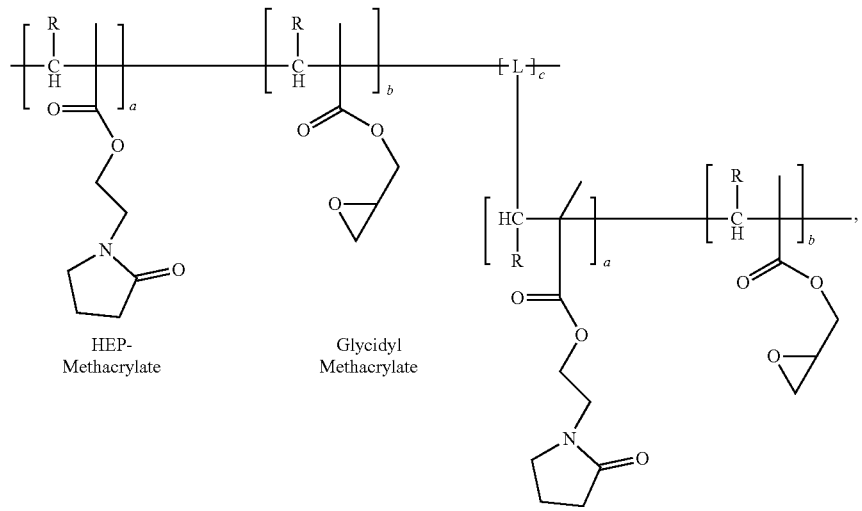

HEP-Methacrylate   Glycidyl Methacrylate

R = H, Aklyl wherein a, b, c are numbers, mole %, the sum of which equals 100 and L is difunctional moiety; or (iii) about 0.1 wt. % to about 30 wt. % of a cross-linked copolymer of hydroxyethylpyrrolidone methacrylate/glyceryl methacrylate covalently linked to a surface-active moiety resulting in the structure:

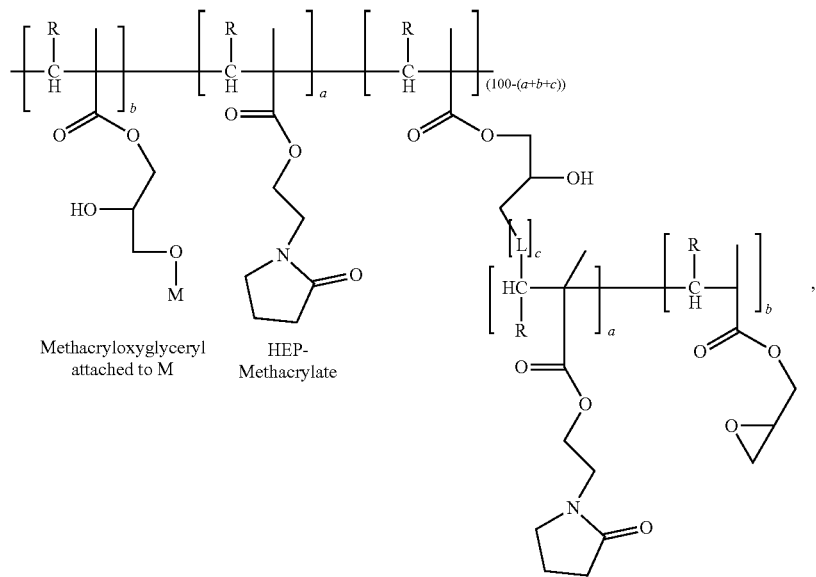

Methacryloxyglyceryl attached to M    HEP-Methacrylate

R = H, Aklyl wherein a, b and c are numbers, mole %, the sum of which is less than 100, M is surface-active moiety, and L is difunctional moiety; or (iv) about 0.1 wt. % to about 30 wt. % of a cross-linked copolymer of hydroxyethylpyrrolidone methacrylate/ glyceryl methacrylate covalently linked to a surface-active moiety resulting in the structure:

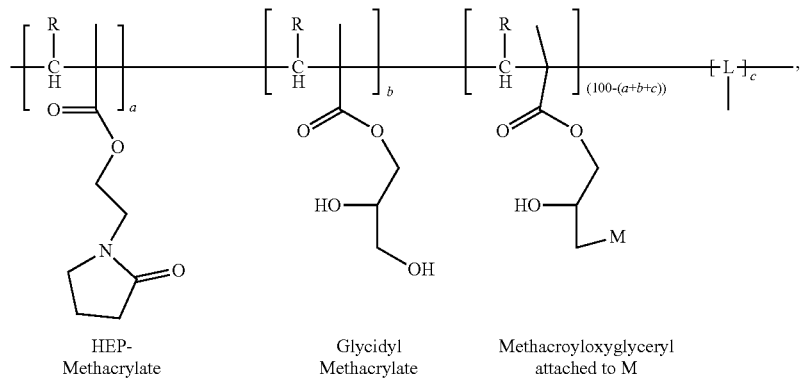

HEP-Methacrylate       Glycidyl Methacrylate       Methacroyloxyglyceryl attached to M R = H, Alkyl wherein a, b and c are numbers, mole %, the sum of which is less than 100, M is surface-active moiety and L is difunctional moiety; and II) about 1 wt. % to about 99 wt. % of at least one additive.

The compositions of the present application can provide a glossy, transparent to matte, opaque finish coating on synthetic films such as polyester, vinyl, polyolefins, and the like, as well as paper and canvas.

Generally, the coating composition has a solids content of about 15-50% and a viscosity of about 200-3000 cps.

The polymer in the coating composition suitably has a K-Value of about 5 to about 100, preferably about 10 to about 70.

The conditions of the thermal activation of the present copolymer, exposure to heat 90-230° C., can be achieved easily by a blow-dryer, flat-iron or curling-iron, or calendering onto the substrate, are selected such that they do not destroy other useful ingredients in the formulation.

When poly-dimethylsiloxane is mixed with an aqueous polymer formulation, the dispersion formed phase-separates into an oily layer and an aqueous layer within minutes. However, when poly-dimethylsiloxane is reacted with the present copolymers, the terminal hydroxyl or amino-functionality of these modified silicones can attach to the epoxy functionality thereby making them more water dispersible and stable as micro-emulsions.

Hair dyes leach from dyed hair over time. The present copolymers can bind hair dyes to hair substrates through covalent bonds that cannot be leached. The present copolymers provide a means to react hair-dyes and printing dyes onto the present copolymers so that when they contain an inorganic or organic OH, SH, NH, or an acidic hydrogen like inorganic and organic acids, or active-hydrogen compounds like Michael-donors or acceptors, or any nucleophilic or electrophilic functionality capable of reacting with the epoxy-functionality, the hair and printing dyes will be permanently bonded to the copolymers. Upon further cross-linking, a crosslinked matrix of active agents and copolymers result in (semi)permanently fixed to the substrate in one step or multiple steps.

The attachment of suitable active agents include; modified silicones, UV-filters, conditioning agents, vitamins, peptides, enzymes, microbiological agents, cleansing agents, fragrances, medical coatings or devices, pharmaceutical actives, oncology agents, therapeutic agents and therapeutic-peptides/polypeptides, dyes, colorants and inks, formation of block-copolymers and hybrid-polymer compositions with other industrially significant polymers and copolymers such as (meth)acrylates and/or (meth)acrylamides, cellulosics, starches, polyesters, polyamides, vinyl-polymers, proteins, guar, poly-olefins and their chemically modified counterparts. Once the active agent is attached to the copolymer, the attachment provides a means to cross-link with other substrates and/or itself, so that it is (semi)permanently attached to the surface of the substrate by a covalent bond, that has a reactive nucleophilic or electrophilic atom within it, and/or can be encased by the crosslinked polymer-active matrix itself.

The conditions for preparing the crosslinkable compositions are very mild and can be performed without the need for specialized equipment or dangerous radiation sources. Addition of other catalysts, such as thermal or photoacids, or thermal/photogenerating radical species, can catalyze the crosslinking reactions by simple exposure to the sun, heat, or other external sources.

Radical, thermal, or chemical crosslinking reactions obviate the problems and issues of high viscosity and uneven application of the crosslinked formulation and the disposal and cleaning of the non-biodegradable crosslinked polymer formulations. When the unused or unreacted composition is simply exposed to water or moisture for several weeks, it renders the reactive epoxy-functionality into a stable non-toxic glycerol moiety so it is ecologically friendly to the environment.

The present application relates to curing or cross-linking or polymerizing a polymerizable material carried out by any appropriate method known in the arts. Insight into curing and cross-linking technology is disclosed in "Thermosetting Polymers," J. P. Pascault et. al. (Marcel Dekker, New York, 2002), which disclosure is incorporated by reference herein.

The polymerization of reactive solution comprising polymerizable polymer can be carried out by employing any of the methods disclosed in "Principles of Polymerization 4th edition," by George Odian (J. Wiley and Sons, Hoboken, New Jersey, 2004), which disclosure is incorporated by reference herein. The preferable techniques or methods employed by the present application to polymerize the polymers would including but not limited to UV-radiation, UV-LED, laser beam, electron beam, gamma irradiation, free-radical, cationic, anionic, thermal, exposure to e-beam and/or by employing a high-energy source in presence of suitable photo initiator for the initiation of polymerization. Suitable sources of radiation include, but are not limited to, mercury, xenon, halogen, carbon arc lamps, sunlight, and radioactive sources.

Polymers in accordance with the present application can be in the form of a powder, solid, liquid, or solution form. Compositions comprising the polymer can be curable via ultra violet (UV) radiation, thermal, electron beam, or gamma irradiation. The polymers can be utilized in the formulation of aqueous, UV curable coatings, or in 100% solid, UV curable coatings. Compositions comprising the polymer can be thermally and/or cationically curable or thermally and/or anionically curable. The polymers or compositions containing the polymers can be thermoplastic polymers that can be produced in either liquid or powder form.

In order to induce polymerization via irradiation, photoinitiators are often incorporated to initiate the polymerization reaction system. Preferable photoinitiators are selected from the following non-limiting group or class of compounds such as 2-hydroxy-2-methyl-1-phenylpropane-1-one, 1-hydroxycyclohexyl phenyl ketone, and 2-methyl-1-[4-(methylthio)phenyl]-2-morphorinopropane-1-on; benzoins e.g. benzyl dimethyl ketal; benzophenones such as benzophenone, 4-phenylbenzophenone, and hydroxybenzophenone; thioxanthones such as isopropylthioxanthone and 2,4-diethylthioxanthone; acylphosphine oxides; and other special initiators such as methyl phenyl glyoxylate; bis[4-(di(4-(2-hydroxyethyl)phenyl)sulfonio)phenyl sulfide], a mixture of bis[4-diphenylsulfonio]phenyl) sulfide bis(hexafluoroantimonate and diphenyl-4-thiophenoxyphenylsulfonium hexafluoroantimonate, bis[4-(di(4-(2-hydroxyethyl)phenyl)sulfonio)phenyl sulfide], 5-2,4-cyclopentadiene-1-yl-[(1,2,3,4,5,6-.eta.)-(1-methylethyl-)benzene]-iron (1+)-hexafluorophosphate(1-)), 4-(2-hydroxytetradecanyloxy) diphenyliodonium hexafluoroantimonate, (4-hydroxynaphtyl) dimethylsulfonium hexafluoroantimonate), photo latent bases such as photo latent diazabicyclo nonene, triphenylsulfonium hexafluorophosphate, triphenylsulfonium hexafluoroantimonate, 4-methoxyphenyldiphenylsulfonium hexafluoroantimonate, 4-methoxyphenyliodonium hexafluoroantimonate, bis(4-tert-butylphenyl)iodonium tetrafluoroborate, (bis(4-tert-butylphenyl)iodonium hexafluorophosphate), (bis(4-tert-phenyl)iodonium hexafluoroantimonate), (bis[4-(diphenylsulfonio)phenyl]sulfide bis(hexafluorophosphate)), aryldiazonium salts, diaryliodonium salts, triarylsulfonium salts, triarylselenonium salts, dialkylphenacylsulfonium salts, triarylsulfoxonium salts, triethanol amine, aryloxydiarylsulfonium salts, and the like for example, triphenylsulfonium hexaflurophosphate, methyidiphenylsulfonium hexafluorophosphate, dimethylphenylsulfonium hexaflurophosphate, diphenyinapththylsulfonium hexaflurophosphate, di(methoxynapththyl)methylsulfonium hexaflurophosphate, (4-octyloxyphenyl) phenyl iodonium hexafluoro antimonate, (4-octyloxyphenyl) diphenyl sulfonium hexafluoro antimonate, (4-decyloxyphenyl) phenyl iodonium hexafluoro antimonite, (4-dodecyloxyphenyl)diphenyl sulfonium hexafluoroantimonate. Preferably, the photoinitiator includes 10-biphenyl-4-yl-2-isopropyl-9H-thixanthen-10-ium hexafurophosphate, 4,4'-dimethyl iodonium hexaflurophosphate, mixed triarylsulfonium hexaflurophosphate salts and reaction products of polyol and 10-(2-carboxymethoxy)-biphenyl-4yl-2-isopropyl-9-oxo-9H-thioxanthen-10-ium hexafluorophosphate. The photoinitiators can be used alone or in combinations thereof. Alternatively, the photoinitiator can be used by mixing it with one or more photopolymerization accelerator, such as a benzoic acid (e.g., 4-dimethylaminobenzoic acid) or a tertiary amine (e.g., diazabicyclo nonene (DBN)), in any appropriate ratio. The photoinitiator is preferably added to the photopolymerizable composition in the range of about 0.1% to about 20% by weight.

In accordance with one embodiment, present application also provides various applications of copolymer of hydroxyethylpyrrolidone methacrylate/glycidyl methacrylate and cross-linked copolymer of hydroxyethylpyrrolidone methacrylate/glycidyl methacrylate in the fields of adhesives, aerosols, agricultural agents, anti-soil redeposition agents, batteries agents, beverages, biocides, cementing and construction agents, cleaning agents, coating agents, conductive materials, cosmetic agents, dental agents, decorated pigments, detergents, dispersants, drugs, electronics, encapsulations, foods, hair sprays, household-industrial institutional, inks and coatings, interlaminate adhesives, lithographic solutions, membrane additive agents, metal working fluids, oilfield agents, paints, paper, paper sizing agents, personal care agents, pharmaceuticals, pigment additives, plasters, plastic, printing, refractive index modifiers, sequestrants, soil release agents, static control agents and wood-care agents.

The polymers of the present application are suitable for use in a wide variety of compositions including industrial, personal care, household, and pharmaceutical applications. Industrial uses include, but are not limited to, formulating inks, flocculation agents, hydrogels, gel forming materials, surface modification agents, coatings, microporous print media, paper sizing additives, shale swell inhibitors, metal coatings, metal working fluids, ceramics, rheology modifiers, reactive biocides, decorated titanium, interlaminate adhesives, agricultural compositions, dispersants, batteries, products comprised of iodine, products comprised of silver, products comprised of carbon and graphene, products comprised of nano carbons, comb/branch polymer adducts, biocidal films, tackifiers, latex weather resistant modifiers, decorated pigments for inks and pastes, decorated cenospheres, decorated barium sulfate, cross-linkers, automotive products and protective films, super-absorbers (i.e., diapers) (see U.S. Pat. Publication No. 2009/0043005A1, the contents of which are hereby incorporated by reference), printing plates, macro-initiating materials, products comprised of graphene, hydrophilic enhancement agents for membranes, anti-fog coatings, polymer blocks, additives to extrudable compounds and films, protective colloidal agents, multi dimensional printing materials including pigments, polymers and inks (for example see WO/2008/077850A2, the contents of which are hereby incorporated by reference), refractive index modifiers, cross-linking agents, microencapsulation particles and additives (see U.S. Pat. No. 5,811, 121 and WO 2007/146722 A1), rheology control agents, grease resistant paper and films, fiber sizing agents, products comprised of alumina, conductive films, cementitious compositions, bioadhesives, tablet coatings, battery binders, resinous UV absorbers (U.S. Pub. No. 20100190947, the contents of which are hereby incorporated by reference), iodine stabilizers, conductive coatings and gels, reactive rheology modifying agents, macro-initiators, coating flex agents, and non-migratory anti-static agents. Personal care and household applications include, but are not limited to, formulating cosmetics, hair care products, oral care and dentifrices, toiletries, hydrogels, laundry products and household cleaning products, and dye absorbent non-woven swatches. Pharmaceutical applications include, but are not limited to, processing aids, medical stents, lubricity modification agents, catheters and other medical device coatings, active ingredient solubilizers, adhesive patches, optical lenses, formulating drug delivery systems, and preparing tablet coatings.

According to one important embodiment of the present application, it is contemplated to employ about 1 wt. % to about 99 wt. % of at least one additive for preparing said compositions of the present application, and wherein, the desired additive required for preparing composition of the present application can vary according to its field of application. Further, a person skilled in the relevant art is aware and capable of picking and choosing of relevant additives required for preparing desired composition as per field of application.

EXAMPLES

The following non-limiting examples are provided to illustrate a few of the methods for preparing following copolymers. The examples are presented for purposes of demonstrating, but not limiting, the preparation of the compounds and compositions of this application.

Example 1

Polyhydroxyethylpyrrolidone Methacrylate/Glycidyl Methacrylate, 95/5 in Acetone

In a 1-L resin kettle equipped with an anchor agitator, thermocouple, gas inlet and reflux condenser, 300 g of acetone was charged into the reactor. The reaction mixture was purged with nitrogen for 30 min. With agitation and nitrogen purging, the reactor was heated to 65° C., then two feeds of 95 g of HEP-Methacrylate and 5 g of Glycidyl Methacrylate (GMA) were fed. HEP-Methacrylate feed was fed over three hours and Glycidyl Methacrylate (GMA) feed was fed over four hours and 0.125 g of Trigonox 25 C75 was charged. After two hours of reaction, 0.125 g of Trigonox 25 C 75 was charged into the reactor. The reaction was held for 2 hours, and then 0.125 g of Trigonox 250 C75 was charged into the reactor. At time 6, 10 and 12 hours, 0.125 g shot of Trigonox 25 C75 was charged into the reactor respectively. After 14 h, the reaction mixture was cooled to room temperature to discharge the product. The Brookfield viscosity of 5% solution at 25° C. was 170 cps using spindle #1 at 10 rpm.

Example 2

Polyhydroxyethylpyrrolidone Methacrylate/Glycidyl Methacrylate, 90/10 in Acetone In a 1-L resin kettle equipped with an anchor agitator, thermocouple, gas inlet and reflux condenser, 300 g of Acetone was charged into the reactor. The reaction mixture was purged with nitrogen for 30 min. With agitation and nitrogen purging, the reactor was heated to 65° C., then two feeds of 90 g of HEP-Methacrylate and 10 g of Glycidyl Methacrylate (GMA) were fed. HEP-Methacrylate feed was fed over three hours and Glycidyl Methacrylate (GMA) feed was fed over four hours and 0.25 g of Trigonox 25 C75 was charged. After two hours of reaction, 0.125 g of Trigonox 25 C 75 was charged into the reactor. The reaction was held for 2 hours, and then 0.125 g of Trigonox 250 C75 was charged into the reactor. At time 6, 10 and 12 hours, 0.125 g shot of Trigonox 25 C75 was charged into the reactor respectively. After 14 h, the reaction mixture was cooled to room temperature and discharged. The Brookfield viscosity of 5% solution in acetone at 25° C. was 100 cps using spindle #1 at 10 rpm.

Example 3

Polyhydroxyethylpyrrolidone Methacrylate/Glycidyl Methacrylate, 80/20 in Acetone In a 1-L resin kettle equipped with an anchor agitator, thermocouple, gas inlet and reflux condenser, 300 g of Acetone was charged into the reactor. The reaction mixture was purged with nitrogen for 30 min. With agitation and nitrogen purging, the reactor was heated to 65° C., then two feeds of 80 g of HEP-Methacrylate and 20 g of Glycidyl Methacrylate (GMA) were fed. HEP-Methacrylate feed was fed over three hours and Glycidyl Methacrylate (GMA) feed was fed over four hours and 0.125 g of Trigonox 25 C75 was charged. After two hours of reaction, 0.125 g of Trigonox 25 C 75 was charged into the reactor. The reaction was held for 2 hours, and then 0.125 g of Trigonox 250 C75 was charged into the reactor. At time 6, 10 and 12 hours, 0.125 g shot of Trigonox 25 C75 was added into the reactor respectively. After 14 h, the reaction mixture was cooled to room temperature and discharged. The Brookfield viscosity of 5% solution in acetone at 25° C. was 150 cps using spindle #1 at 10 rpm.

Example 4

Polyhydroxyethylpyrrolidone Methacrylate/Glycidyl Methacrylate, 99/1 in Acetone

In a 1-L resin kettle equipped with an anchor agitator, thermocouple, gas inlet and reflux condenser, 250 g of Acetone was charged into the reactor. The reaction mixture was purged with nitrogen for 30 min. With agitation and nitrogen purging, the reactor was heated to 65° C., then two feeds of 99 g of HEP-Methacrylate and 1 g of Glycidyl Methacrylate (GMA) mixed with 50 g acetone were fed. HEP-Methacrylate feed was fed over a period of three hours and Glycidyl Methacrylate (GMA) feed was fed over four hours and 0.125 g of Trigonox 25 C75 was charged. After two hours of reaction, 0.125 g of Trigonox 25 C 75 was charged into the reactor. The reaction was held for 2 hours, and then 0.125 g of Trigonox 250 C75 was charged into the reactor. At time 6, 10 and 12 hours, 0.125 g of Trigonox 25 C75 added into the reactor respectively. After 14 h, the reaction mixture was cooled to room temperature and discharged. The Brookfield viscosity of 5% solution in acetone at 25° C. was 200 cps using spindle #1 at 10 rpm.

Example 5

Polyhydroxyethylpyrrolidone Methacrylate/Glycidyl Methacrylate, Pentaerythritol Triacrylate 90/10/0.5) in Acetone In a 1-L resin kettle equipped with an anchor agitator, thermocouple, gas inlet and reflux condenser, 300 g of Acetone can be charged into the reactor. The reaction mixture can be purged with nitrogen for 30 min. With agitation and nitrogen purging, the reactor is heated to 65° C., then two feeds were added as Feed-1: of 90 g of HEP-Methacrylate containing 0.5% pentaerythritol triacrylate (PETA), and Feed-2: 30 g of Glycidyl Methacrylate (GMA) are fed. HEP-Methacrylate/pentaerythritol triacrylate (PETA), feed is fed over three hours and Glycidyl Methacrylate (GMA) feed is fed over four hours and 0.25 g of Trigonox 25 C75 is charged. After two hours of reaction, 0.125 g of Trigonox 25 C 75 is charged into the reactor. The reaction is held for 2 hours, and then 0.125 g of Trigonox 250 C75 is charged into the reactor. At time 6, 10 and 12 hours, 0.125 g shot of Trigonox 25 C75 is charged into the reactor respectively. After 14 h, the reaction slurry is stripped of acetone to yield a white powdery product.

Example 6

Illustrative Example of Polymer-Polysaccharide Hybrid: (Polyhydroxyethylpyrrolidone-Methacrylate/Glycidyl Methacrylate/Carboxymethyl Cellulose) in Water/t-Butanol

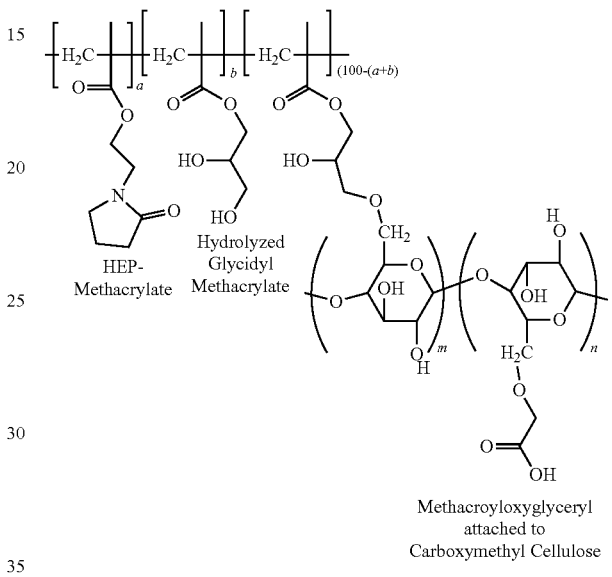

Methacroyloxyglyceryl attached to Carboxymethyl Cellulose 100 g of Hydroxyethyl-pyrrolidone methacrylate-GMA (95:5) of Example 1 was dissolved in 150 ml water at 25° C. and then added a slurry containing 200 g Carboxymethyl Cellulose (Blanose) in 200 g t-butanol, and added 1 g phosphoric acid 85% and stirred rapidly at 450 rpm and heated to 85° C. for 16 hours. Then the slurry was cooled and filtered and washed three times with 500 g t-butanol, three times with 500 g acetone, and dried. FT-IR confirmed the presence of Hydroxyethyl-pyrrolidone methacrylate by the presence of the 1680 cm$^{-1}$ band and CMC by the 1600 and 1050 cm$^{-1}$ bands. Yield is 300 g.

The above surface modified composition provides benefits of a flexible pyrrolidone functionality with excellent biocompatibility and toxicological properties of pyrrolidone, film-formation, disintegrant excipienecy, adhesiveness, dye-mordant, complexation to a variety of substrates, binder, and potentially enhanced biostability conferred to CMC against viscosity loss by enzymatic processes, along with the thickening power and rheological properties of nontoxic CMC, emulsion stabilization, lubricant, dispersant, disintegrant, fixative, sizing-agent, kinetic inhibitor of tartrate precipitation in chilled beverages, and binder capabilities of CMC in one compact molecule. Synergies between the pyrrolidone and cellulose functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production to just name a few.

Example 7

Illustrative Example of Polymer-Polysaccharide Hybrid: (Polyhydroxyethylpyrrolidone-Methacrylate/Glycidyl Methacrylate/Hydroxyethyl Cellulose) in Water

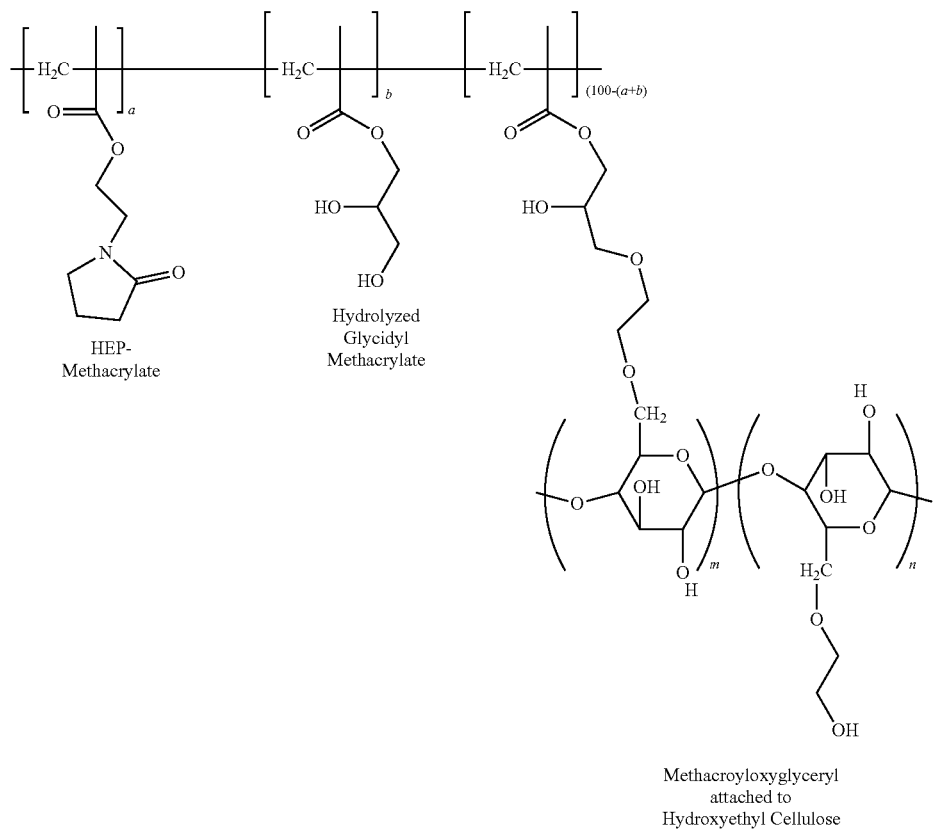

60 g of Hydroxyethyl-pyrrolidone methacrylate-GMA (95:5) was dissolved in 200 ml of water at 25° C. and then added 60 g high viscosity Hydroxyethyl Cellulose (250HV), and added 1 g phosphoric acid 85% and stirred rapidly at 450 rpm at 25° C. for 1 hour. Then the reaction mixture was dried into a powder under vacuum. FT-IR confirmed the presence of Hydroxyethyl-pyrrolidone methacrylate by the presence of the 1680 $cm^{-1}$ band and HEC by the 1050 $cm^{-1}$ band. Yield is 110 g corresponding to 92% of theoretical.

The above surface modified composition provides the benefits of a flexible pyrrolidone functionality with excellent biocompatibility and toxicological properties of pyrrolidone, film-formation, disintegrant excipienecy, adhesiveness, dye-mordant, complexation to a variety of substrates, binder, and potentially enhanced biostability conferred to HEC against viscosity loss by enzymatic processes, along with the thickening power and rheological properties of nontoxic HEC, emulsion stabilization, lubricant, dispersant, disintegrant, fixative, sizing-agent, kinetic inhibitor of tartrate precipitation in chilled beverages, and binder capabilities of HEC in one compact molecule. Synergies between the pyrrolidone and cellulose functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 8

Illustrative Example of Polymer-Polysaccharide Hybrid: (Polyhydroxyethylpyrrolidone-Methacrylate/Glycidyl Methacrylate/Hydroxypropyl Cellulose) in Water/t-Butanol

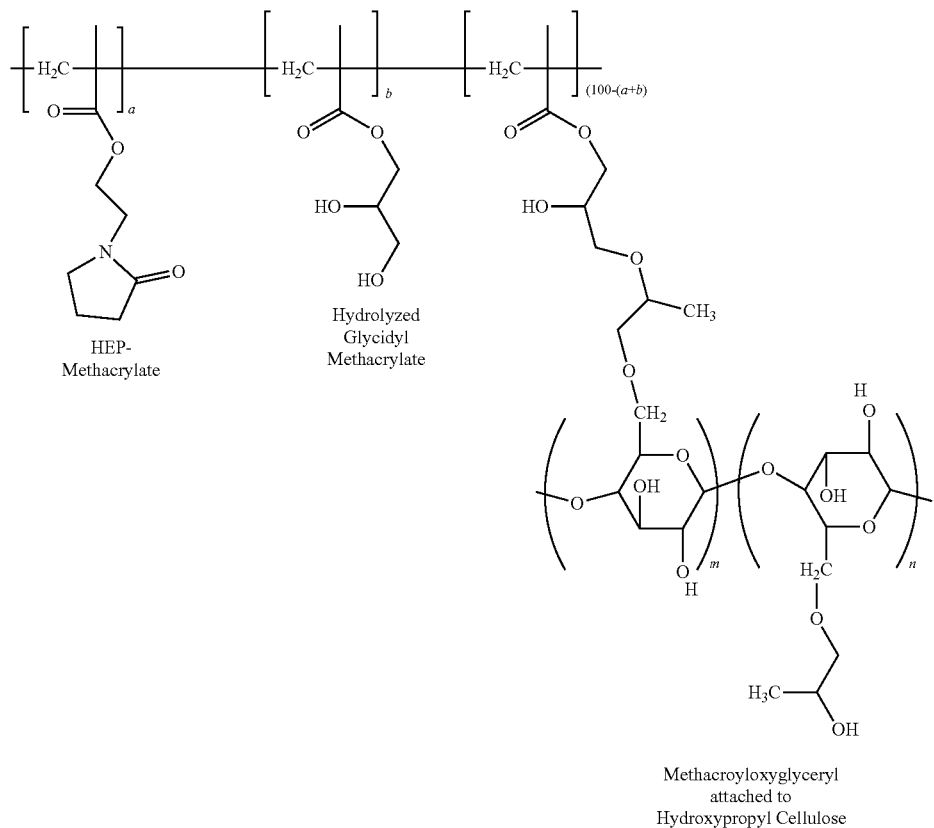

Methacroyloxyglyceryl attached to Hydroxypropyl Cellulose 50 g of Hydroxyethyl-pyrrolidone methacrylate-GMA (95:5) was dissolved in 200 ml of water at 25° C. and then added 50 g Hydroxypropyl Cellulose (HF-Pharma), and added 1 g phosphoric acid 85% and stirred rapidly at 450 rpm at 25° C. for 1 hour. Then the reaction mixture was dried into a powder under vacuum. FT-IR confirmed the presence of Hydroxyethyl-pyrrolidone methacrylate by the presence of the 1680 cm$^{-1}$ band and HPC by the 1050 cm$^{-1}$ band. Yield is 110 g corresponding to 99% of theoretical with 10% moisture.

The above surface modified composition provides the benefits of a flexible pyrrolidone functionality with excellent biocompatibility and toxicological properties of pyrrolidone, film-formation, disintegrant excipienecy, adhesiveness, dye-mordant, complexation to a variety of substrates, binder, and potentially enhanced biostability conferred to HPC against viscosity loss by enzymatic processes, HPC, emulsion stabilizer, lubricant, dispersant, excipient, a thermo-responsive polymer, and binder capabilities of HPC in one compact molecule. Synergies between the pyrrolidone and cellulose functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 9

Illustrative Example of Polymer-Hydrophobically Modified Polysaccharide Hybrid: (Polyhydroxyethylpyrrolidone-Methacrylate/Glycidyl Methacrylate/Hydroxypropyl Cellulose-Stearate) in t-Butanol

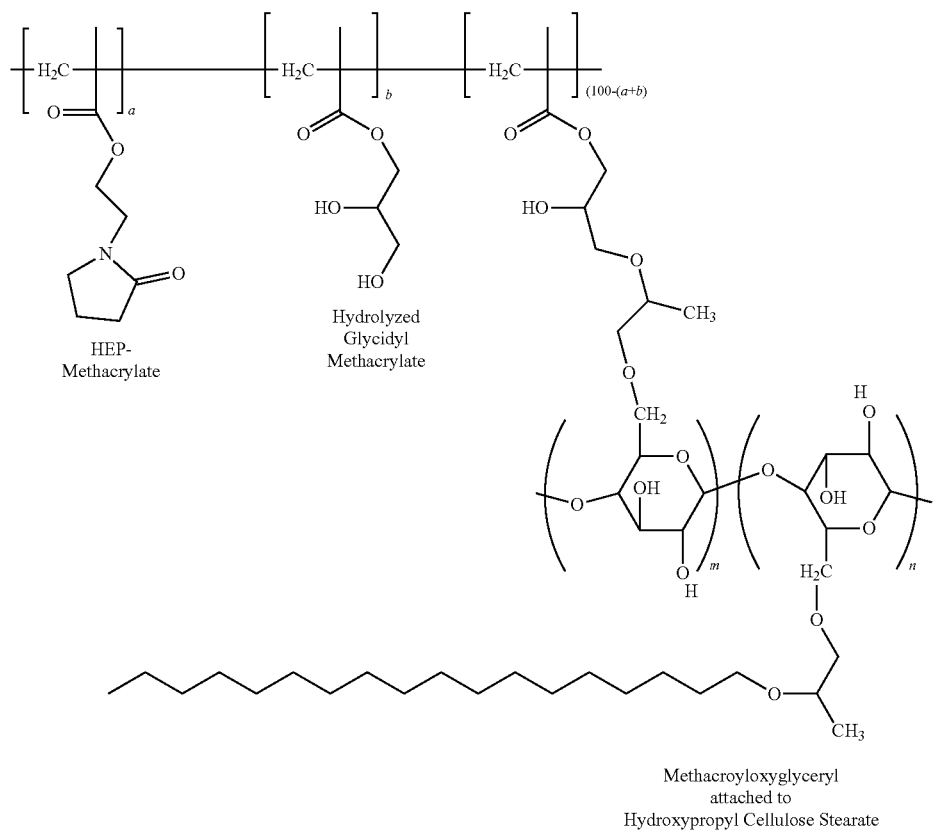

Methacroyloxyglyceryl attached to Hydroxypropyl Cellulose Stearate 10 g of Hydroxyethyl-pyrrolidone methacrylate-GMA-HPC from example 7 was reacted with 1 g stearic acid-methyl ester in 50 g t-butanol at 85° C. for 16 hours. Then the reaction mixture was dried into a powder under vacuum. FT-IR confirmed the presence of Hydroxyethyl-pyrrolidone methacrylate by the presence of the 1680 $cm^{-1}$ band and HPC by the 1050 $cm^{-1}$ band and the Stearate functionality by the 1740 $cm^{-1}$ band. Yield is 11 g corresponding to 99% of theoretical. Then 0.5 g of reaction product was dispersed into 20 ml water to generate a milky dispersion that swelled into a slightly hazy hydrogel overnight.

The above surface modified composition provides the benefits of a flexible pyrrolidone functionality with excellent biocompatibility and toxicological properties of pyrrolidone, film-formation, disintegrant excipienecy, adhesiveness, dye-mordant, complexation to a variety of substrates, binder, and potentially enhanced biostability conferred to HPC against viscosity loss by enzymatic processes, an emulsion stabilizer, lubricant, dispersant, surfactant, excipient, a thermo-responsive polymer, and binder capabilities of HPC in one compact molecule. Synergies between the pyrrolidone and cellulose functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 10

Illustrative Example of a Polymer-Biofunctional Peptide/Protein Hybrid: (Polyhydroxyethylpyrrolidone-Methacrylate/Glycidyl Methacrylate/Poly-(l)-Lysine) in 25:75 Acetone/Water

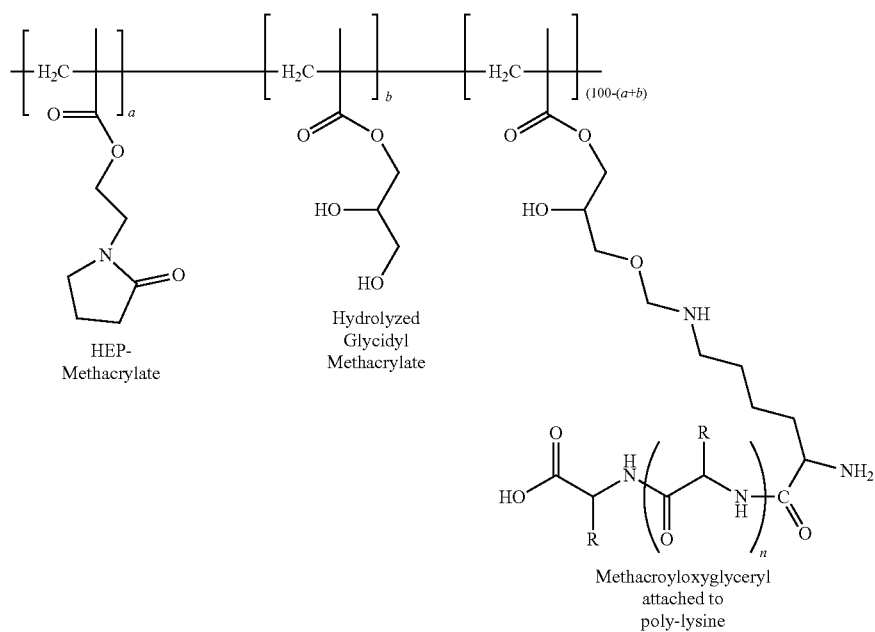

HEP-Methacrylate

Hydrolyzed Glycidyl Methacrylate

Methacroyloxyglyceryl attached to poly-lysine 15 g (4.8 mM) of Hydroxyethyl-pyrrolidone methacrylate-GMA (95:5)(0.32 mM/g) was dissolved into 85 g acetone. Separately, 22.8 g Poly(l)-Lysine (M. wt.=4751) (0.21 mM/g) was dissolved into 300 g water and neutralized with 200 mg NaOH. Then added HEPMA/GMA solution into Poly-(1)-Lysine solution and mixed thoroughly. A mild exotherm was noticed (=5C) indicating the reaction was proceeding. Then heated reaction mixture to 50° C. for 2 hrs, and then ramped up to 85° C. and held at this temperature for an additional 16 hours. Then the reaction mixture was dried into a powder under vacuum. FT-IR confirmed the presence of Hydroxyethyl-pyrrolidone methacrylate by the presence of the ester 1722 $cm^{-1}$ band and the Poly-Lysine functionality by the 1556 $cm^{-1}$ band. Yield is 37 g corresponding to 98% of theoretical.

The above surface modified composition provides the benefits of a flexible pyrrolidone functionality with all its inherent properties with that of a biofunctional peptide/protein. This hybrid can exhibit enhanced stability against proteolytic enzymes, improved conformational stability to retain its activity, unique solubility characteristics, utility in vaccine production, therapeutics, antimicrobial properties, utility in recombinant DNA/RNA technologies, gene-therapy, and enhanced pharmacokinetic properties. Synergies between the pyrrolidone and peptide/protein functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 11

Illustrative Example of a Polymer-Silicon Hybrid: (Polyhydroxyethylpyrrolidone-Methacrylate/Glycidyl Methacrylate/Poly-(Aminopropyl)-Dimethylsiloxane) in t-ButOH

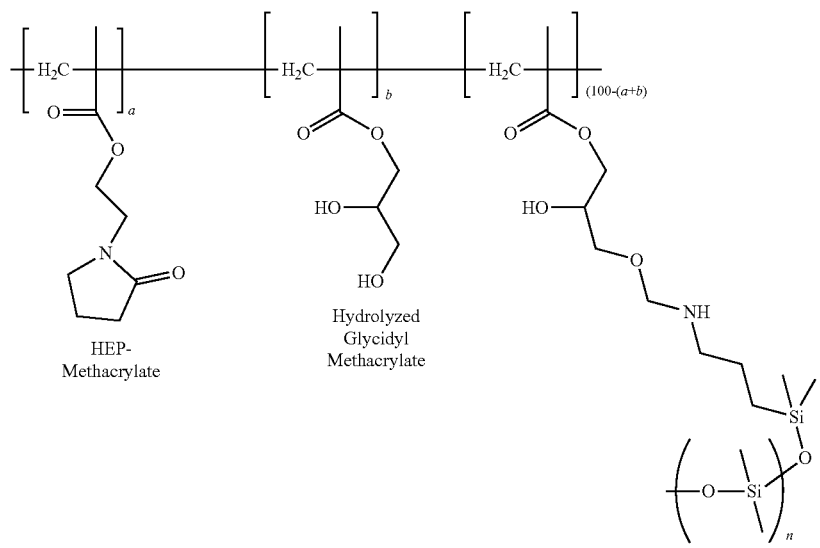

Methacroyloxyglyceryl attached to Aminopropyl poly-dimethyl siloxane 15 g (4.8 mM) of Hydroxyethyl-pyrrolidone methacrylate-GMA (95:5) (0.32 mM/g) was dissolved into 85 g t-ButOH. Separately, 21.8 g Poly(siloxane/aminopropylmethylsiloxane) (0.227 meq/g) was dissolved into 100 g t-butanol. Then added HEPMA/GMA solution into Polyaminosiloxane solution and mixed thoroughly. Then heated reaction mixture to 85° C. for 16 hrs. Then the reaction mixture was dried into an oily residue under vacuum. FT-IR confirmed the presence of Hydroxyethyl-pyrrolidone methacrylate by the presence of the ester 1728 and 1667 $cm^{-1}$ band and the Poly-aminosiloxane functionality by the 1091, 1021, and 805 $cm^{-1}$ bands. Yield is 36 g corresponding to 98% of theoretical. Then 0.5 g of reaction product was dispersed into 20 ml water to generate a milky dispersion.

The above surface modified composition provides the benefits of a flexible pyrrolidone functionality with all its inherent properties with that of a silicone, particularly known for its unusual rheological (or flow) properties. PDMS is optically clear, and, in general, inert, non-toxic, and non-flammable. Its applications range from contact lenses and medical devices to elastomers; it is also present in shampoos as a conditioner that makes hair shiny and slippery, a sizing-agent, in food (antifoaming agent), caulking, and lubricants. Synergies between the pyrrolidone and peptide/protein functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 12

Illustrative Example of a Polymer-Polyether Hybrid: (Polyhydroxyethylpyrrolidone-Methacrylate/Glycidyl Methacrylate/Aminoethyl-Polyethylene Glycol in t-ButOH

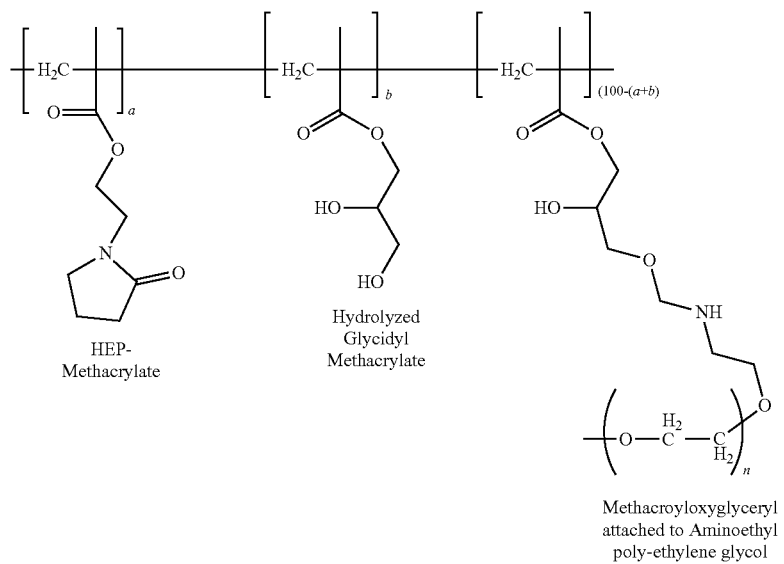

10.26 g (3.3 mM) of Hydroxyethyl-pyrrolidone methacrylate-GMA (95:5) (0.32 mM/g) was dissolved into 85 g t-ButOH. Separately, 5 g (3.3 meq) Poly(aminoethyl-PEG Mn=3000)(0.66 meq/g) was dissolved into 100 g t-butanol. Then added HEPMA/GMA solution into Poly(aminoethyl)-PEG solution and mixed thoroughly. Then heated reaction mixture to 85° C. for 16 hrs. Then the reaction mixture was dried into a waxy residue under vacuum. FT-IR confirmed the presence of Hydroxyethyl-pyrrolidone methacrylate by the presence of the ester 1728 and 1667 $cm^{-1}$ band and the Poly(aminoethyl)-PEG functionality by the 1103 $cm^{-1}$ band. Yield is 15 g corresponding to 96% of theoretical.

The above surface modified composition provides the benefits of a flexible pyrrolidone functionality with all its inherent properties with that of a polyether, particularly known for its surfactant properties. In general, PEG is inert, and non-toxic. PEG and its higher molecular weight counterpart PEO, find use in different applications, and have different physical properties (e.g. viscosity) due to chain length, but their chemical properties are nearly identical. They vary in consistency from liquid to solid, depending on the molecular weight. Branched, star, and comb-PEGS are also well known leading to difference in viscosity as well as its architecture.

Its applications range from sizing agents, molds, dispersants, contact lenses and medical devices to elastomers, lubricants, laxatives, anti-foaming agent in foods, useful in electronics, binder, and an excipient. Synergies between the pyrrolidone and PEG functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 13

Illustrative Example of a Polymer-Polyether Hybrid: (Polyhydroxyethylpyrrolidone-Methacrylate/Glycidyl Methacrylate/Aminopropyl-Polypropylene Glycol in t-ButOH

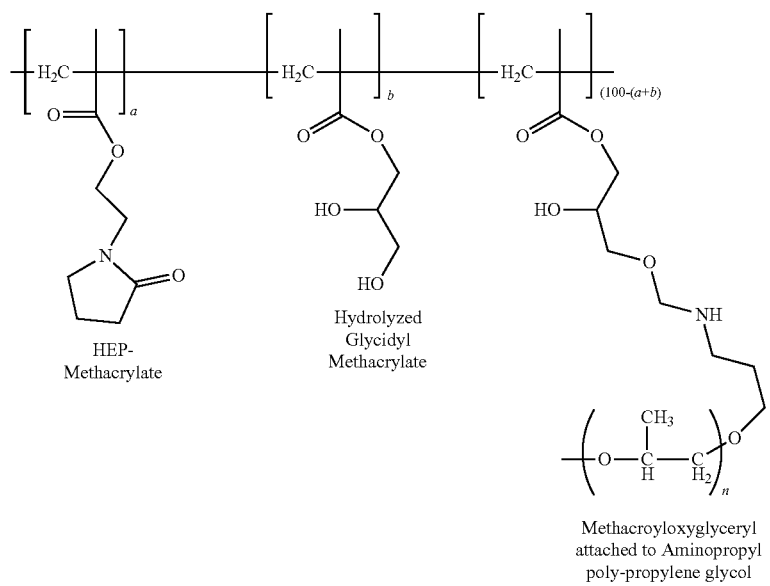

15 g (4.8 mM) of Hydroxyethyl-pyrrolidone methacrylate-GMA (95:5)(0.32 mM/g) was dissolved into 85 g t-BuOH. Separately, 2.9 g (4.8 meq) Poly(aminopropyl-PPG Mn=600)(1.66 meq/g) was dissolved into 100 g t-butanol. Then added HEPMA/GMA solution into Poly(aminopropyl)-PPG solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1720 and 1670 cm$^{-1}$ band and the Poly(aminopropyl)-PPG functionality by the 1070 cm$^{-1}$ band. Yield is 17 g corresponding to 95% of theoretical.

The above surface modified composition provides the benefits of a flexible pyrrolidone functionality with all its inherent properties with that of a polyether, particularly known for its surfactant properties. In general, PPG is inert, and non-toxic. PEG and its higher molecular weight counterpart PPO, find use in different applications, in which as the chain length increases, its solubility in water decreases. They vary in consistency from liquid to solid, depending on the molecular weight.

Its applications range from a rheological modifier, sizing agents, surfactant, wetting-agent, dispersants, lubricants, laxatives, binder, and an excipient. Synergies between the pyrrolidone and PEG functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production

Example 14

Illustrative Example of a Polymer-Poly-Amino-Saccharide Hybrid: (Polyhydroxyethylpyrrolidone-Methacrylate/Glycidyl Methacrylate/Deacetylated-Chitosan in DMF/Water (1:1)

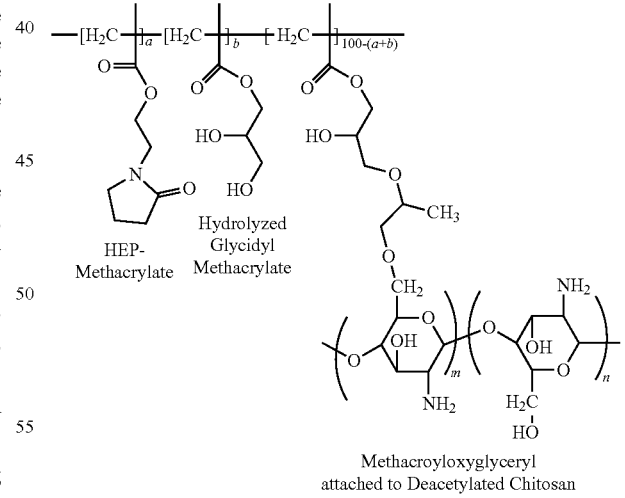

0.1 g (0.032 mM) of Hydroxyethyl-pyrrolidone methacrylate-GMA (95:5)(0.32 mM/g) was dissolved into 10 g solution of DMF/water (1:1). Separately, 6.04 g (0.032 meq) 80% deacetylated-Chitosan with a molecular weight of 50,000-190,000 Da (5.3 ueq/g) was dissolved into 200 g DMF/water (1:1). Then added HEPMA/GMA solution into Chitosan solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1720 and 1670 cm$^{-1}$ band and the Chitosan functionality by the 1078 cm$^{-1}$ band. Yield is 6 g corresponding to 86% of theoretical.

The above surface modified composition provides the benefits of a flexible pyrrolidone functionality with all its inherent properties with that of a poly-amino-saccharide that has unique properties such as being a non-toxic, anti-bacterial, hydrophobic, biodegradable, and a biocompatible polymer.

Its applications range from medicine, wastewater treatment, biomembranes, hydrogels, carrier for drug delivery, as a mucoadhesive, wound dressings, and tissue engineering scaffolds, enhanced hydrophilicity and mechanical properties, improve blood compatibility, or enhanced antibacterial properties. Another useful application is in the synthesis of chitosan nanoparticles for targeted drug release. For this application, synthetic polymers have been used to enhance either the synthesis process or the properties of the resulting nanoparticles. Synergies between the pyrrolidone and chitosan functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 15

Illustrative Example of a Polymer-Drug Hybrid: (Polyhydroxyethylpyrrolidone-Methacrylate/Glycidyl Methacrylate/Dopamine in THF

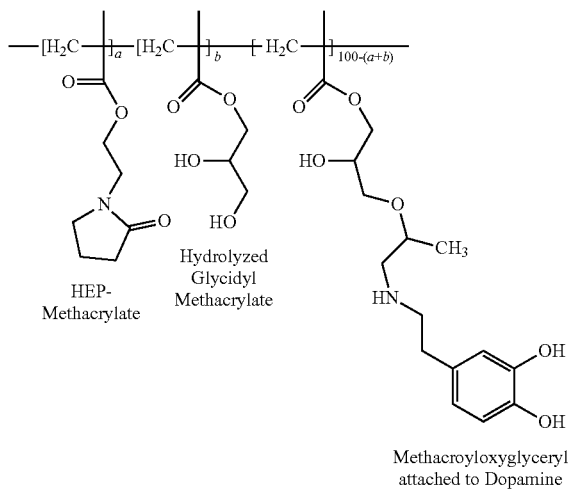

Methacroyloxyglyceryl attached to Dopamine 15 g (4.8 mM) of Hydroxyethyl-pyrrolidone methacrylate-GMA (95:5)(0.32 mM/g) was dissolved into 85 g THF. Separately, 0.74 g (4.8 mM) Dopamine (6.5 meq/g) was dissolved into 100 g THF. Then added HEPMA/GMA solution into Dopamine solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1720 and 1680 cm$^{-1}$ band and the Dopamine functionality by the 1631 cm$^{-1}$ band. Yield is 15 g corresponding to 96% of theoretical.

This polymer-drug conjugate provides the benefits of a flexible pyrrolidone functionality with all its inherent properties with that of a bioactive drug, with biocompatibility, and potentially enhanced pharmokentics, biostability, lower toxicity, and enhanced blood circulation levels.

Its applications can range from medicine, hydrogels, carrier for drug delivery, opiate-induced drug therapy, as a mucoadhesive, wound dressings, enhanced hydrophilicity and mechanical properties, improve blood compatibility, or nanoparticles for targeted drug release. Synergies between the pyrrolidone and chitosan functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 16

Illustrative Example of a Polymer-Polyester Hybrid: (Polyhydroxyethylpyrrolidone-Methacrylate/Glycidyl Methacrylate/Poly-Lactide-co-Glycolide in THF

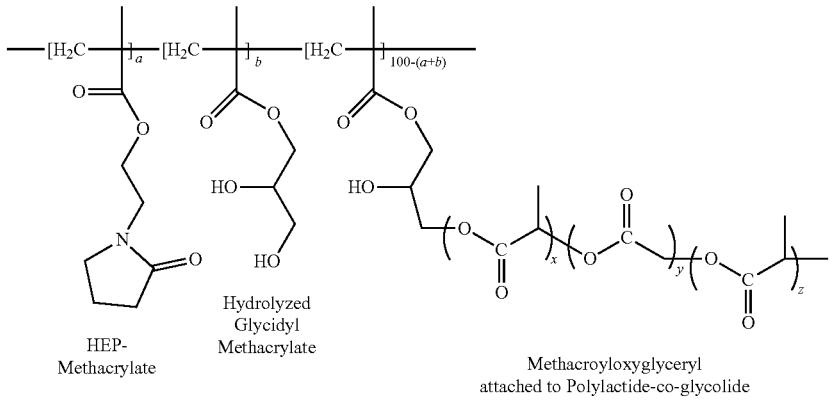

Methacroyloxyglyceryl attached to Polylactide-co-glycolide 1.0 g(0.32 mM) of Hydroxyethyl-pyrrolidone methacrylate-GMA (95:5) (0.32 mM/g) was dissolved into 85 g THF. Separately, 12.3 g (0.32 mM) Poly(lactide-co-glycolide) with a molecular weight of 24,000-38,000 Da (26 ueq/g) was dissolved into 100 g THF. Then added HEPMA/GMA solution into Poly(lactide-co-glycolide) solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1720 and 1680 $cm^{-1}$ band and the Poly(lactide-co-glycolide) functionality by the 929 $cm^{-1}$ band. Yield is 11 g corresponding to 83% of theoretical.

The above surface modified composition provides the benefits of a flexible pyrrolidone functionality with all its inherent properties with that of a polylactide/polyglycolide that is biodegradable and a bioactive thermoplastic aliphatic polyester derived from renewable resources, such as corn starch, tapioca roots, or starch, or sugarcane.

Its applications can range from medicine, hydrogels, carrier for drug delivery, or nanoparticles for targeted drug release, implantable medical devices; including rings, pins, rods, plates and screws, tissue engineering scaffolds, shrink wraps and biodegradable disposable packaging, disposable tableware, upholstery, disposable garments, awnings, feminine hygiene products, absorbable sutures, and diapers. Synergies between the pyrrolidone and chitosan functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 17

Illustrative Example of a Polymer-DNA/RNA Hybrid: (Polyhydroxyethylpyrrolidone-Methacrylate/Glycidyl Methacrylate/Adenosine in THF

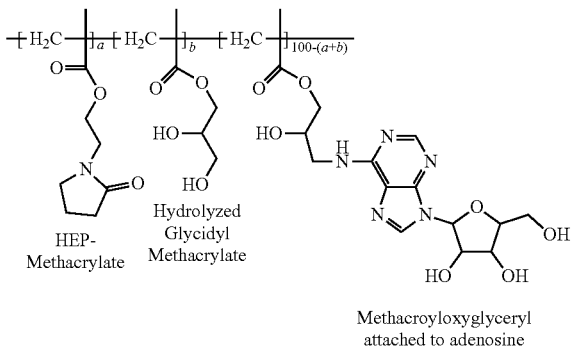

15 g (4.8 mM) of Hydroxyethyl-pyrrolidone methacrylate-GMA (95:5)(0.32 mM/g) was dissolved into 85 g THF. Separately, 1.28 g (4.8 mM) Adenosine (3.75 meq/g) was dissolved into 100 g THF. Then added HEPMA/GMA solution into Adenosine solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 $cm^{-1}$ band and the Adenosine functionality by the 1110 $cm^{-1}$ band. Yield is 16 g corresponding to 95% of theoretical.

The above surface modified composition provides the benefits of a flexible pyrrolidone functionality with all its inherent properties with that of a DNA or RNA conjugate. Its applications can range from gene therapy, medicine, nanobiotechnology, antisense-mediated gene expression, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 18

Illustrative Example of a Polymer-Maleic Anhydride Copolymer Hybrid: (Polyhydroxyethylpyrrolidone-Methacrylate/Glycidyl Methacrylate/(Maleic Anhydride/MVE Copolymer) in Acetone

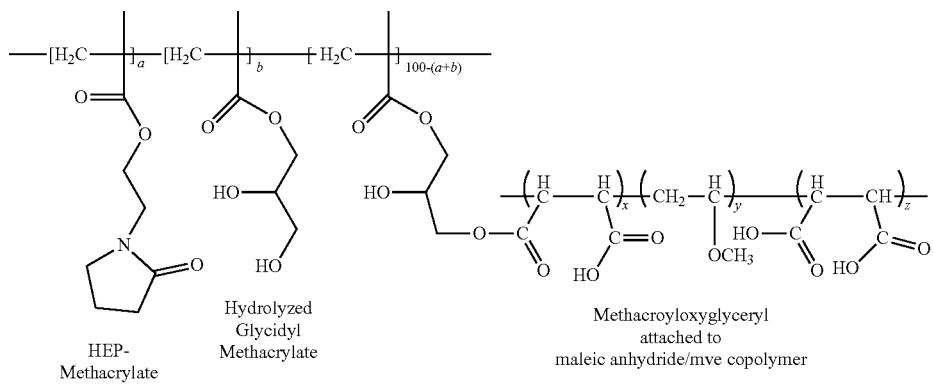

15 g (4.8 mM) of Hydroxyethyl-pyrrolidone methacrylate-GMA (95:5)(0.32 mM/g) was dissolved into 85 g Acetone. Separately, 154 g of Poly-(maleic anhydride-co-methylvinyl ether) copolymer (6.5 meq/g) was dissolved into 300 g Acetone. Then added HEPMA/GMA solution into Poly-(maleic anhydride-co-methylvinyl ether) copolymer solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 cm$^{-1}$ band and the Poly-(maleic anhydride-co-methylvinyl ether) copolymer functionality by the 1780 cm$^{-1}$ band. Yield is 160 g corresponding to 95% of theoretical.

The above surface modified composition provides the benefits of a flexible pyrrolidone functionality with all its inherent properties with that of a reactive maleic anhydride copolymer that can form acids, salts, esters, amides, amic acids, and imide functionalities. The anhydride functionality can be used to graft any moiety that has a reactive nitrogen, oxygen, carbon, or sulfur atom on it. Its applications can range from medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 19

Illustrative Example of a Polymer-Maleic Anhydride Copolymer Hybrid: (Polyhydroxyethylpyrrolidone-Methacrylate/Glycidyl Methacrylate/Crosslinked (Maleic Anhydride/MVE Copolymer) in Acetone

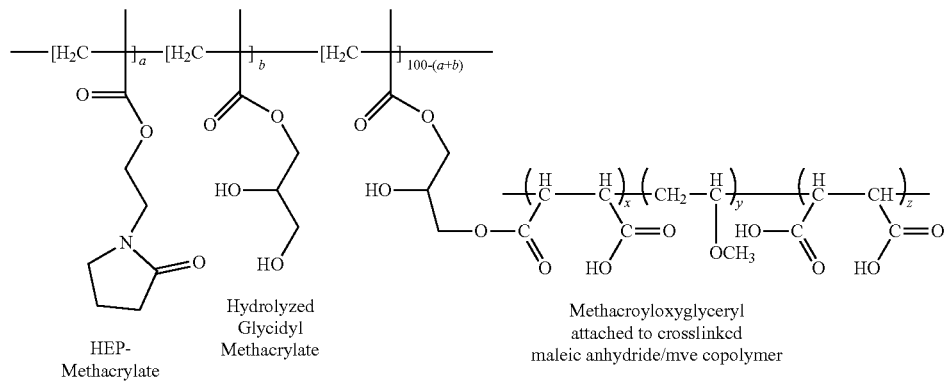

15 g (4.8 mM) of Hydroxyethyl-pyrrolidone methacrylate-GMA (95:5)(0.32 mM/g) was dissolved into 85 g Acetone. Separately, 154 g of crosslinked Poly-(maleic anhydride-co-methylvinyl ether/decadiene) copolymer (6.5 meq/g) was dispersed into 300 g Acetone. Then added HEPMA/GMA solution into Poly-(maleic anhydride-co-methylvinyl ether/decadiene) copolymer slurry and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 cm$^{-1}$ band and the Poly-(maleic anhydride-co-methylvinyl ether/decadiene) copolymer functionality by the 1780 cm$^{-1}$ band. Yield is 150 g corresponding to 89% of theoretical.

The above surface modified composition provides the same benefits as its soluble counterpart above in example 17, that includes the benefits of a flexible pyrrolidone functionality with all its inherent properties with that of a reactive maleic anhydride copolymer that is also a rheological modifier/thickener, and that can form acids, salts, esters, amides, amic acids, and imide functionalities. The anhydride functionality can be used to graft any moiety that has a reactive nitrogen, oxygen, carbon, or sulfur atom on it. Its applications can range from medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 20

Illustrative Example of a Polymer-Maleic Anhydride Copolymer Hybrid: (Polyhydroxyethylpyrrolidone-Methacrylate/Glycidyl Methacrylate/(Styrene/Maleic Anhydride) Copolymer in Acetone

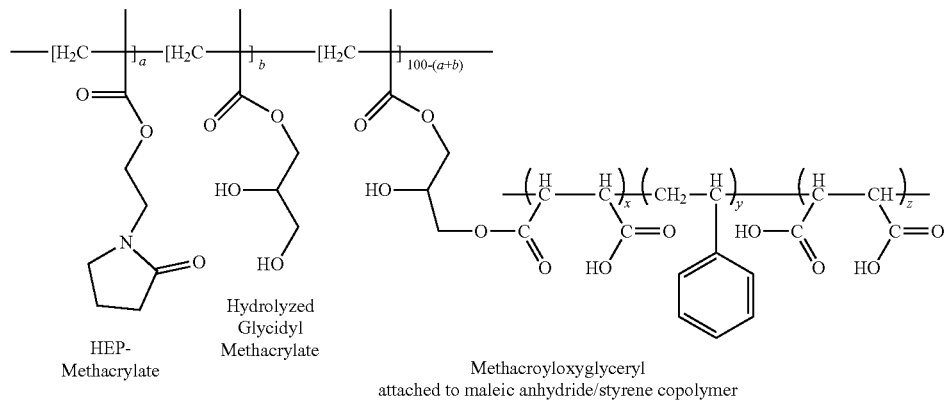

15 g (4.8 mM) of Hydroxyethyl-pyrrolidone methacrylate-GMA (95:5)(0.32 mM/g) was dissolved into 85 g Acetone. Separately, 154 g of Poly-(styrene/maleic anhydride) copolymer (5.0-0.05 meq/g) was dissolved into 300 g Acetone. Then added HEPMA/GMA solution into Poly-(styrene/maleic anhydride) copolymer solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 $cm^{-1}$ band and the Poly-(styrene/maleic anhydride) copolymer functionality by the 1780 $cm^{-1}$ band. Yield is 155 g corresponding to 92% of theoretical.

The above surface modified composition provides the benefits of a flexible pyrrolidone functionality with all its inherent properties with that of a reactive maleic anhydride copolymer that is hydrophobic, stiff, and UV absorbing, and that can form acids, salts, esters, amides, amic acids, and imide functionalities. The anhydride functionality can be used to graft any moiety that has a reactive nitrogen, oxygen, carbon, or sulfur atom on it. Its applications can range from medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 21

Illustrative Example of a Polymer-Maleic Anhydride Copolymer Hybrid: (Polyhydroxyethylpyrrolidone-Methacrylate/Glycidyl Methacrylate/Olefin/Maleic Anhydride Copolymer in Acetone

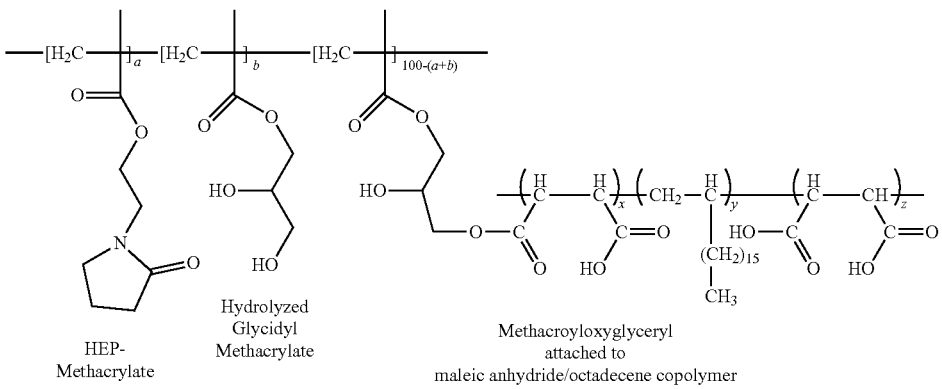

15 g (4.8 mM) of Hydroxyethyl-pyrrolidone methacrylate-GMA (95:5)(0.32 mM/g) was dissolved into 85 g Acetone. Separately, 354 g of Poly-(octadecene/maleic anhydride) copolymer (2.9 meq/g) was dissolved into 400 g Acetone. Then added HEPMA/GMA solution into Poly-(octadecene/maleic anhydride) copolymer solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 $cm^{-1}$ band and the Poly-(octadecene/maleic anhydride) copolymer functionality by the 1780 $cm^{-1}$ band. Yield is 350 g corresponding to 95% of theoretical.

The above surface modified composition provides the benefits of a flexible pyrrolidone functionality with all its inherent properties with that of a reactive maleic anhydride copolymer that is extremely hydrophobic, oil-soluble, flexible, and that can form acids, salts, esters, amides, amic acids, and imide functionalities. The anhydride functionality can be used to graft any moiety that has a reactive nitrogen, oxygen, carbon, or sulfur atom on it. Its applications can range from medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 22

Illustrative Example of a Polymer-Maleic Anhydride Copolymer Hybrid: (Polyhydroxyethylpyrrolidone-Methacrylate/Glycidyl Methacrylate/(Maleic Anhydride/Isobutylene Copolymer) in Acetone/Ethanol

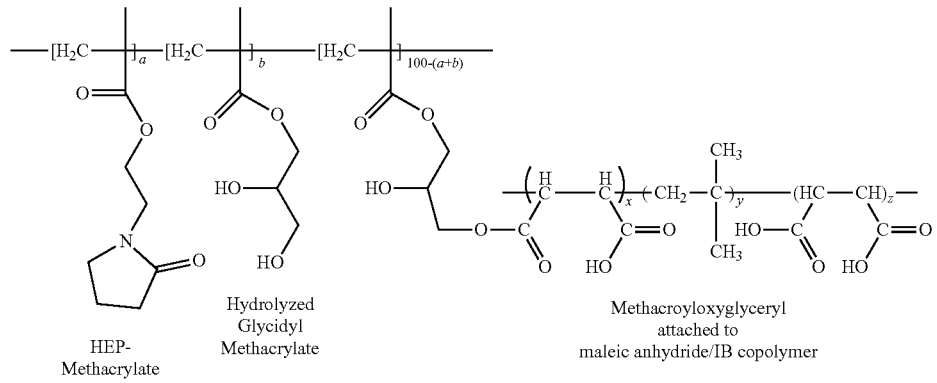

HEP-Methacrylate

Hydrolyzed Glycidyl Methacrylate

Methacroyloxyglyceryl attached to maleic anhydride/IB copolymer 15 g (4.8 mM) of Hydroxyethyl-pyrrolidone methacrylate-GMA (95:5)(0.32 mM/g) was dissolved into 85 g Acetone. Separately, 154 g of partially prehydrolyzed or esterified Poly-(maleic anhydride-co-isobutylene) copolymer (6.5 meq/g) was dispersed into 300 g ethanol. Then added HEPMA/GMA solution into Poly-(maleic anhydride-co-isobutylene) copolymer solution and mixed thoroughly with 1% concentrated sulfuric acid. Then heated reaction mixture to 110° C. for 16 hrs. Then the reaction mixture was dried into a powder under vacuum. FT-IR confirmed the presence of Hydroxyethyl-pyrrolidone methacrylate by the presence of the ester 1730 and 1660 $cm^{-1}$ band and the Poly-(maleic anhydride-co-isobutylene) copolymer functionality by the 1780 $cm^{-1}$ band. Yield is 160 g corresponding to 95% of theoretical.

The above surface modified composition provides the benefits of a flexible pyrrolidone functionality with all its inherent properties with that of a reactive maleic anhydride copolymer that can form acids, salts, esters, amides, amic acids, and imide functionalities. The anhydride functionality can be used to graft any moiety that has a reactive nitrogen, oxygen, carbon, or sulfur atom on it. Its applications can range from medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 23

Illustrative Example of a Polymer-Reactive Methacrylate Copolymer Hybrid: (Polyhydroxyethylpyrrolidone-Methacrylate/Glycidyl Methacrylate/Mono-2-(Methacryloyloxy)ethyl Succinate in Acetone

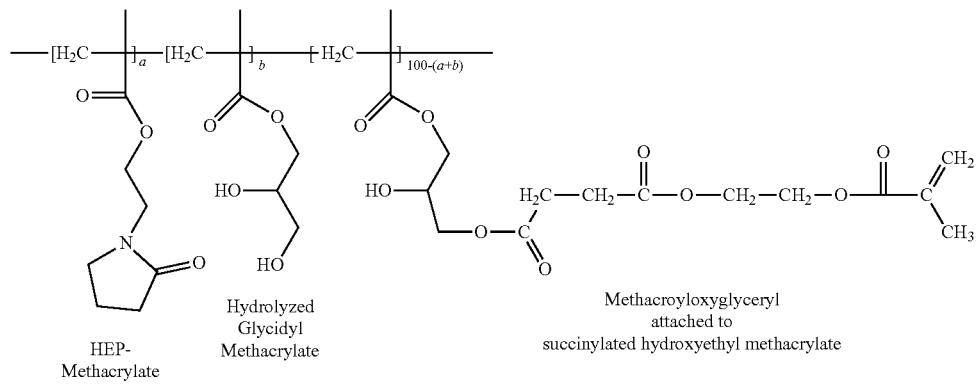

HEP-Methacrylate

Hydrolyzed Glycidyl Methacrylate

Methacroyloxyglyceryl attached to succinylated hydroxyethyl methacrylate 15 g (4.8 mM) of Hydroxyethyl-pyrrolidone methacrylate-GMA (95:5)(0.32 mM/g) was dissolved into 85 g Acetone. Separately, 1.1 g (4.8 mM) of mono-2-(Methacryloyloxy)ethyl succinate (4.3 meq/g) was dissolved into 10 g Acetone. Then added HEPMA/GMA solution into mono-2-(Methacryloyloxy)ethyl succinate solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 cm$^{-1}$ band and the mono-2-(Methacryloyloxy) ethyl succinate functionality by the 1610 cm$^{-1}$ band. Yield is 16 g corresponding to 99% of theoretical.

The above surface modified composition the benefits of a flexible pyrrolidone functionality with all its inherent properties with that of a reactive double bond that's UV-curable, or photocurable, or radically curable to form a crosslinked block copolymer system, or a branched block copolymer system with a radically polymerizable monomer. These monomers include acrylates, methacrylates, acrylamides, methacrylamides, vinyl formamide, vinyl pyrrolidone, vinyl caprolactam, vinyl imidazole, vinyl acetate, ethylene, alpha-olefins from C3-C30 that are linear, or branched, or cyclic, vinyl sulfonics, vinyl phosphoric acids, styrene, methyl styrene, acrylonitrile, methacrylonitrile, butadiene, allyl amines, dimethyl diallyl ammonium chlorides, vinyl carbonates, PEG-acrylates and methacrylates, vinyl ethers, maleic anhydride, itaconates, crotonates, vinyl esters, allyl alcohols, isoprene, butylenes, vinyl butyral, vinyl halogens, vinyl cinnamate, vinyl formal, vinylidene halogens, vinyl methyl ketone, vinyl napthalenes, vinyl pyridines, acrylamidopropyl sulfonic acids/salts, and or combinations thereof. Its applications can range from post-polymerizable coatings, UV curable coatings, e-beam, gamma-radiation curable, photocurable coatings, medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 24

Illustrative Example of a Polymer-Reactive Acrylate Copolymer Hybrid: (Polyhydroxyethylpyrrolidone-Methacrylate/Glycidyl Methacrylate/Mono-2-(Acryloyloxy)Ethyl Succinate in Acetone

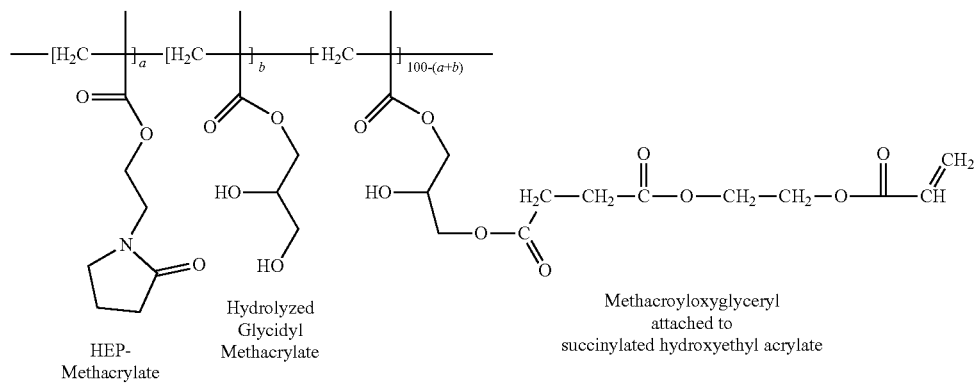

15 g (4.8 mM) of Hydroxyethyl-pyrrolidone methacrylate-GMA (95:5)(0.32 mM/g) was dissolved into 85 g Acetone. Separately, 1.0 g (4.8 mM) of mono-2-(Acryloyloxy)ethyl succinate (4.6 meq/g) was dissolved into 10 g Acetone. Then added HEPMA/GMA solution into mono-2-(Acryloyloxy)ethyl succinate solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 $cm^{-1}$ band and the mono-2-(Acryloyloxy)ethyl succinate functionality by the 1605 $cm^{-1}$ band. Yield is 15 g corresponding to 94% of theoretical.

The above surface modified composition provides the benefits of a flexible pyrrolidone functionality with all its inherent properties with that of a reactive double bond that's UV-curable, or photocurable, or radically curable to form a crosslinked block copolymer system, or a branched block copolymer system with a radically polymerizable monomer. These monomers include acrylates, methacrylates, acrylamides, methacrylamides, vinyl formamide, vinyl pyrrolidone, vinyl caprolactam, vinyl imidazole, vinyl acetate, ethylene, alpha-olefins from $C_3$-$C_{30}$ that are linear, or branched, or cyclic, vinyl sulfonics, vinyl phosphoric acids, styrene, methyl styrene, acrylonitrile, methacrylonitrile, butadiene, allyl amines, dimethyl diallyl ammonium chlorides, vinyl carbonates, PEG-acrylates and methacrylates, vinyl ethers, maleic anhydride, itaconates, crotonates, vinyl esters, allyl alcohols, isoprene, butylenes, vinyl butyral, vinyl halogens, vinyl cinnamate, vinyl formal, vinylidene halogens, vinyl methyl ketone, vinyl napthalenes, vinyl pyridines, acrylamidopropyl sulfonic acids/salts, and or combinations thereof. Its applications can range from post-polymerizable coatings, UV curable coatings, e-beam, gamma-radiation curable, photocurable coatings, medicine, nanobiotechnology, nanostructured self-assemblies, and diagnostic reagents. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 25

Illustrative Example of a Polymer-Polyvinyl Alcohol Copolymer Hybrid: (Polyhydroxyethylpyrrolidone-Methacrylate/Glycidyl Methacrylate/Polyvinyl Alcohol in Water

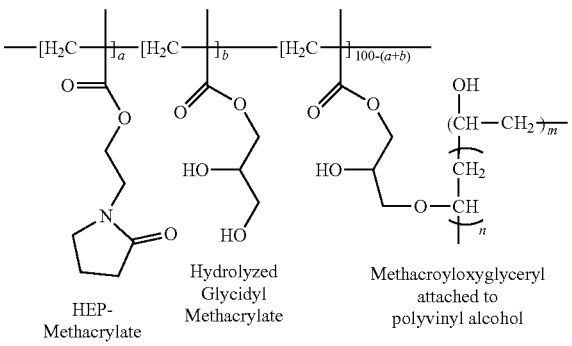

15 g (4.8 mM) of Hydroxyethyl-pyrrolidone methacrylate-GMA (95:5)(0.32 mM/g) was dissolved into 85 g water. Separately, 150 g of Polyvinyl alcohol (22.7 meq/g) was dissolved into 300 g water. Then added HEPMA/GMA solution into Polyvinyl alcohol solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 $cm^{-1}$ band and the Polyvinyl alcohol functionality by the 1025 $cm^{-1}$ band. Yield is 150 g corresponding to 91% of theoretical.

The above surface modified composition provides the benefits of a flexible pyrrolidone functionality with all its inherent properties with that of a poly-alcohol that exhibits excellent film forming capabilities, emulsifying, oil and grease resistant, high tensile strength and flexibility, adhesive properties, and high oxygen barrier properties.

Its applications can range from medicine, hydrogels, carrier for drug delivery, or nanoparticles for targeted drug release, implantable medical devices, tissue engineering scaffolds, Synergies between the pyrrolidone and polyalcohol functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 26

Illustrative Example of a Polymer-Polyvinyl Alcohol Copolymer Hybrid: (Polyhydroxyethylpyrrolidone-Methacrylate/Glycidyl Methacrylate/Polyhydroxyethyl Methacrylate in t-ButOH

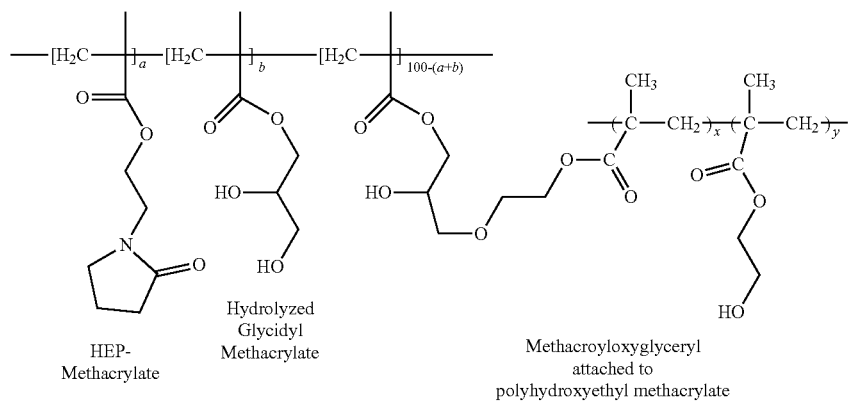

HEP-Methacrylate

Hydrolyzed Glycidyl Methacrylate

Methacroyloxyglyceryl attached to polyhydroxyethyl methacrylate 15 g (4.8 mM) of Hydroxyethyl-pyrrolidone methacrylate-GMA (95:5)(0.32 mM/g) was dissolved into 85 g t-butanol. Separately, 150 g of Polyhydroxyethyl methacrylate (7.7 meq/g) was dissolved into 300 g t-butanol. Then added HEPMA/GMA solution into Polyhydroxyethyl methacrylate solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 cm$^{-1}$ band and the Polyhydroxyethyl methacrylate functionality by the 1180 cm$^{-1}$ band. Yield is 140 g corresponding to 88% of theoretical.

The above surface modified composition copolymer provides the benefits of a flexible pyrrolidone functionality with all its inherent properties with that of a poly-ester/alcohol that exhibits excellent film forming capabilities, adhesive properties, and high oxygen transfer properties.

Its applications can range from medicine, hydrogels, contact lens materials, carrier for drug delivery, or nanoparticles for targeted drug release, tissue engineering scaffolds, Synergies between the pyrrolidone and poly-ester/alcohol functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 27

Illustrative Example of a Polymer-Polyurethane Copolymer Hybrid: (Polyhydroxyethylpyrrolidone-Methacrylate/Glycidyl Methacrylate/Polyurethane Prepolymer in THF

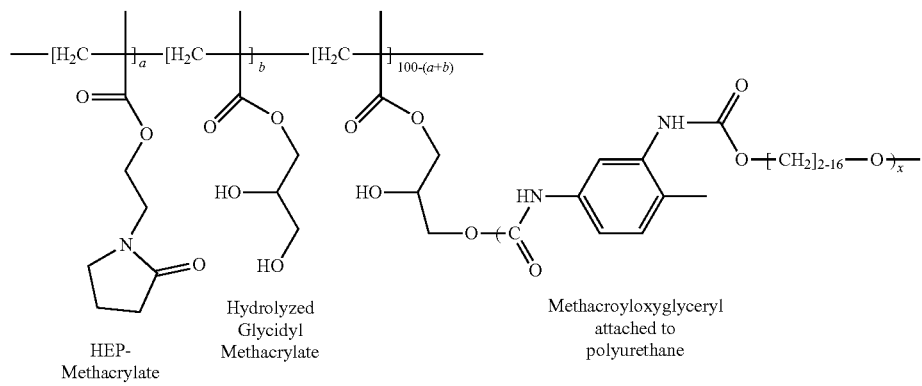

HEP-Methacrylate | Hydrolyzed Glycidyl Methacrylate | Methacroyloxyglyceryl attached to polyurethane 15 g (4.8 mM) of Hydroxyethyl-pyrrolidone methacrylate-GMA (95:5)(0.32 mM/g) was dissolved into 85 g THF. Separately, 5.8 g of diisocyanate-terminated Poly(toluene diisocyanate/ethylene glycol 1:2 eq) prepolymer (0.82 meq/g) with a molecular weight of 2440 daltons was dissolved into 100 g THF. Then added a partially hydrolyzed HEPMA/GMA solution into Polyurethane-prepolymer solution and mixed thoroughly. Then heated reaction mixture to 85° C. for 16 hrs. Then the reaction mixture was dried into a powder under vacuum. FT-IR confirmed the presence of Hydroxyethyl-pyrrolidone methacrylate by the presence of the ester 1730 and 1660 cm$^{-1}$ band and the Polyurethane-prepolymer functionality by the 1528 cm$^{-1}$ band. Yield is 20 g corresponding to 96% of theoretical.

The above surface modified composition provides the benefits of a flexible pyrrolidone functionality with all its inherent properties with that of a polyurethane that exhibits thermosetting/thermoplastic behavior, excellent film forming capabilities, biodegradable, and adhesive properties.

Its applications can range from medicine, hydrogels, construction materials, foams, high performance adhesives, surface coatings and surface sealants, synthetic fibers, carpet underlay, hard-plastic parts, condoms, and hoses. tissue engineering scaffolds, Synergies between the pyrrolidone and polyurethane functionalities are envisioned as well. This can find utility in pharmaceutical applications like enhanced drug delivery, excipiency, biostability, adhesiveness to a variety substrates thereby providing surface-modification, unique solubilities in solvents, and surface-activeness, and utility in a variety of applications in medicine, pharmacy, cosmetics and industrial production.

Example 28

High Dielectric Constant Material

Employing the teachings of U.S. Pat. No. 7,264,876 and Chem. Phys. Let. 342 (2001) pp. 265-271 (the contents of which are hereby incorporated by reference) as a guide for the production of a high dielectric constant material comprised of wrapped single-wall carbon nanotubes (SWNT), the following formulation can be designed:

SWNT materials can be dispersed in 1% sodium dodecyl sulfate (SDS) in water at a concentration of 50 mg/l by a combination of high-shear mixing and sufficient ultrasonication. In this example, enough HEP-Methacrylate (M06)/Glycidyl Methacrylate (GMA) (Example 3) would be added to the mixture to result in a 1% solution by weight.

Example 29

Reactive Protective Colloidal Agent

Employing the teachings of U.S. Pat. No. 3,997,306 (the contents of which are hereby incorporated by reference), as a guide for the production of a microencapsulated particle, the following process was designed:

An electrophoretic medium internal phase (hydrocarbon containing titania and carbon black particles) can be emulsified in water in the presence of HEP-Methacrylate (M06)/Glycidyl Methacrylate (GMA) (Example 3) for one hour with mechanical agitation to form a hydrocarbon-in-water emulsion. To this emulsion, there can be added dropwise an aqueous solution of polyethyleneimine (PEI), with continued mechanical agitation. The reaction would be allowed to proceed for 15 minutes after the addition of the PEI had been completed and the resultant capsules would be separated from the liquid by centrifugation.

Example 30

Functional Silica Particle

Employing amine or carboxyl functionalized silica microspheres, referencing Technical Data Sheet 635 from Polysciences, the contents of which are hereby incorporated by reference, enables the covalent attachment of HEP-Methacrylate (M06)/Glycidyl Methacrylate (GMA) (Example 3) to the surface of the silica particle. Note that suitable catalysts for this reaction are identified in Chapter 5 of the Lee & Neville Epoxy Handbook, the contents of which are hereby incorporated by reference. Representative chemical structures are below:

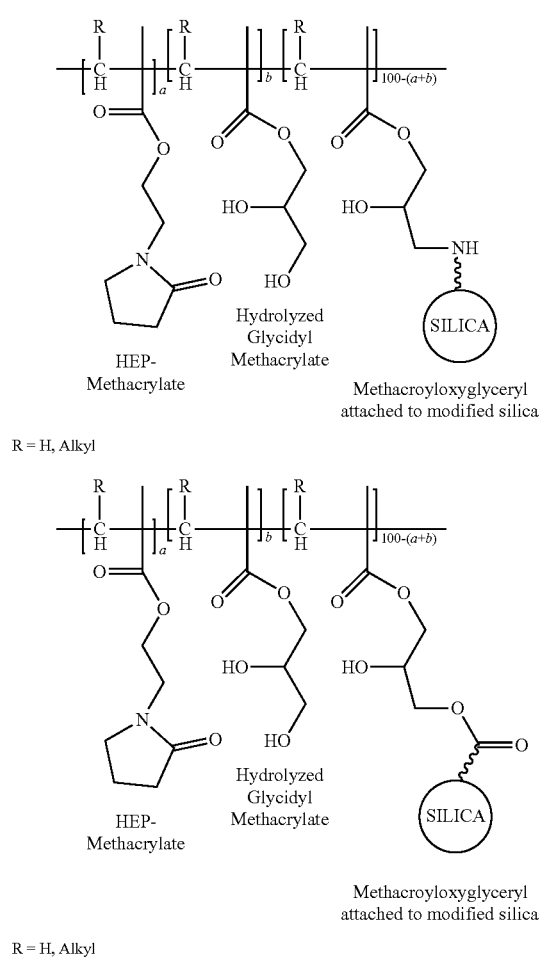

Example 31

Fiber Sizing Agent Additive

Employing the teachings of U.S. Pat. No. 3,997,306 (the contents of which are hereby incorporated by reference), specifically Example 2 in '306, as a guide for the production of a sizing agent, the following formulation can be designed:

| Ingredient | Grams/liter |
| --- | --- |
| EPON 828 | 19.19 (1.92) |
| Reaction product of partial ester of maleic anhydride and monomethyl ether of polyethylene glycol reacted with 3,4 epoxycyclohexane carboxylate | 3.19 (0.32) |
| Industriol FC-180 | 2.38 (0.24) |
| Emulphor 719 | 2.38 (0.24) |
| Igepal CA-630 | 1.32 (0.13) |
| Alpha-methacrytoxypropyltriethoxysilane | 1.08 (0.11) |
| Alpha-aminopropyltriethoxysilane | 3.27 (0.33) |
| Emery 6717 | 0.55 (0.06) |
| Polyhydroxyethylpyrrolidone-methacrylate/ glycidyl methacrylate/polysiloxane (Example 11) | 9.61 (0.96) |
| Water | Dilute to 1 liter |

Example 32

Cementious Composition

Employing the teachings of U.S. Pat. No. 4,048,077 (the contents of which are hereby incorporated by reference), specifically Example 2 in '077, as a guide for the production of a cementious composition, in this case a drilling mud, the following formulation can be designed:

To samples having a content of 4% of bentonite in water practically free from electrolytes and having a loss in water occurring without the use of additives according to API of 24 cm3 0.4% of carboxymethyl cellulose of medium viscosity (CMC-MV) and 0.1% of (Polyhydroxyethylpyrrolidone-methacrylate/glycidyl methacrylate/Hydroxypropyl Cellulose-Stearate) (Example 9) would be added. The losses in water of the samples would be measured (a) according to API under normal conditions (20° C.) and (b) after a 15 hours' aging at 200° C.

Example 33

Battery Binding Composition

Employing the teachings of U.S. Pat. No. 6,242,133 B1 (the contents of which are hereby incorporated by reference) as a guide for the production of a battery binding composition, the following formulation can be designed:

In preparation of the electrode, 3.0 wt % aqueous solution of cobalt chloride (CoCl2) as a transition metal salt based on the weight of the hydrogen absorbing alloy can be added to 3.0 wt % of polyvinyl alcohol (PVA) and 3.0 wt % of HEP-Methacrylate (M06)/Glycidyl Methacrylate (GMA) (Example 3), based on the weight of the hydrogen absorbing ally, as a binder and the hydrogen absorbing alloy and binder would be mixed to prepare a paste. The paste would be coated and filled on both sides of a 0.8 mm thick punched metal nickel plate as an electrically conductive substrate to prepare an hydrogen absorbing alloy electrode.

Example 34

UV Absorber Composition

In an amber or dark reaction flask equipped with agitation, 10 g of HEP-Methacrylate (M06)/Glycidyl Methacrylate (GMA) (Example 3), copolymer in water (20% solids) can be added. Then 0.1 g of 4-aminobenzophenone can be added. The solution is heated to 40° C. for one hour. Then 0.1 g of DMAPMA can be added and the solution is heated at 40° C. for an additional hour. Note that suitable catalysts for these steps of the reaction are identified in Chapter 5 of the Lee & Neville Epoxy Handbook. A representative structure for the reaction product is presented below

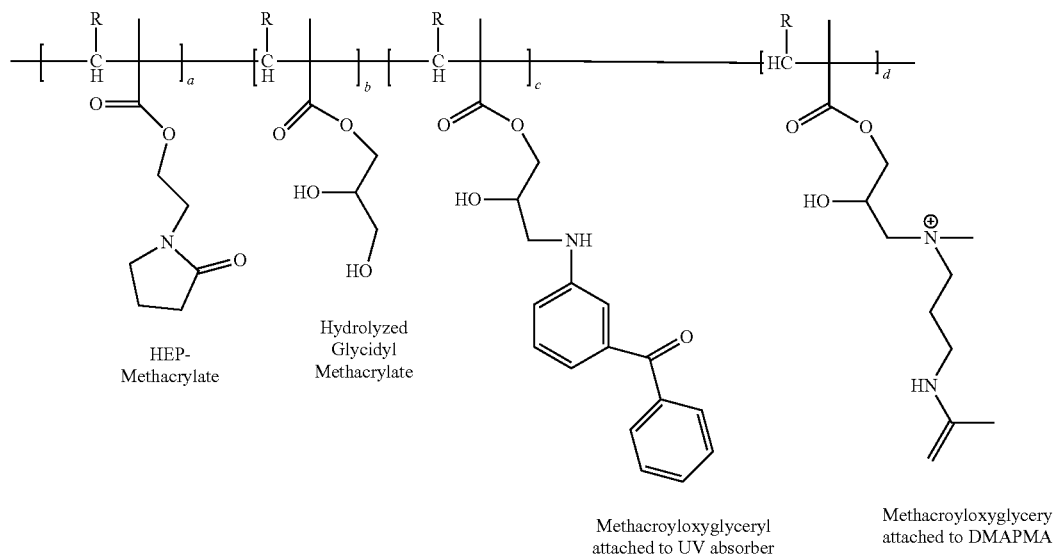

R = H, Alkyl

Example 35

Photo-Initiator Composition

Using the teachings of WO 2005/076074 A2, a polymeric photo-initiator is constructed. In an amber or dark reaction flask equipped with agitation, 10 g of HEP-Methacrylate (M06)/Glycidyl Methacrylate (GMA) (Example 3), copolymer in acetone (20% solids) can be added. Then 0.1 g of 2-benzyl-1-{4-[(2-hydroxyethyl)-acryloyl-amino]phenyl}-2-dimethylamino-1-butanone is added. The solution can be heated at 40° C. for one hour. Then 0.1 g of DMAPMA is added. The solution can be heated at 40° C. for one hour. Note that suitable catalysts for these steps of the reaction are identified in Chapter 5 of the Lee & Neville Epoxy Handbook. A representative structure for the reaction product is presented below:

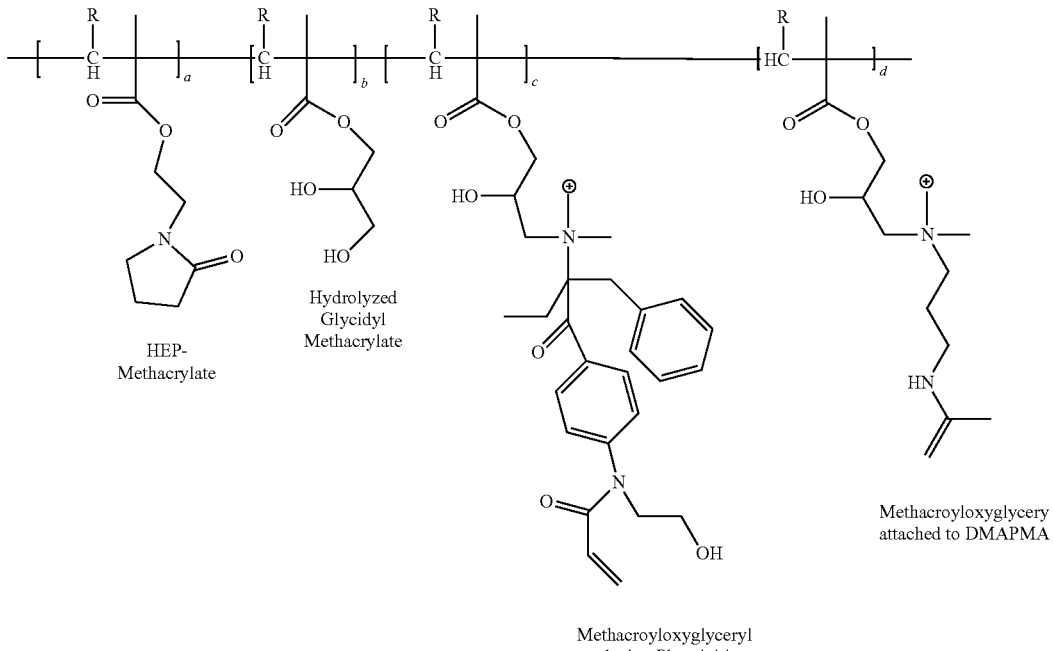

R = H, Alkyl

Example 36

UV Curable Ink

Employing the teachings of U.S. Pat. Appl. No 2008/0225099 A1 (the contents of which are hereby incorporated by reference) as a guide for the production of a UV curable ink composition, the following formulation can be designed:

| Ingredients | Wt % |
| --- | --- |
| Craynor 435, Polyether Acrylate Oligomer | 13.0 |
| SR 508, Dipropylene Glycol Diacrylate | 60.7 |
| SR 285, Tetrahydrofurfuryl acrylate | 10.0 |
| V-Caprolactam | 2.5 |
| HEP-Methacrylate (M06)/Glycidyl Methacrylate (GMA) (Example 3) | 2.0 |
| IRG 379 | 2.0 |
| IRG 819 | 2.0 |
| Darocur ITX | 2.0s |
| Base 2621K | 7.9 |
| Hyper Blue #DW10629 | 0.1 |
| TEGO Rad 2200 N | 0.2 |

While a number of embodiments of this invention have been represented, it was apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example

What is claimed is:

1. A composition comprising:
   i) a copolymer of hydroxyethylpyrrolidone methacrylate/glycidyl methacrylate having a structure:

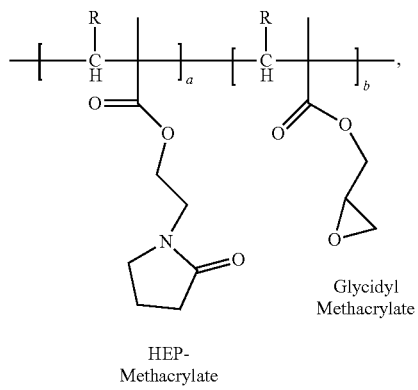

R = H, Alkyl and
   ii) one or more surface-active moiety, wherein the surface-active moiety is selected from the group consisting of:
      a. organic moieties selected from the group consisting of: natural moieties selected from the group consisting of a biofunctional peptide, protein, glycol-protein, lipo-protein, polypeptide, DNA, RNA, and a pharmaceutical active, synthetic moieties selected from the group consisting of maleic anhydride-copolymer, itaconic anhydride copolymer, maleic acid-copolymer, itaconic acid-copolymer, polyterphtalate, polyalkyd, polyester, polyurethane, polyether, epoxy, nylon, poly(meth)acrylate, polyolefin, polyvinyl ether, polystyrene, poly-vinyl-substituted-monomer, poly(meth)acrylamide, polyethyleneglycol, polypropyleneglycol, polysiloxane, polydimethylsiloxane, silicone polymer, polysulfone, polyamide, polylactam, a pharmaceutical active, a sunscreen active and; and/or
      b. modified allotrope moieties selected from the group consisting of modified graphene, modified fullerenes, modified carbon nanotube, modified graphite, and modified carbon black;

wherein R is hydrogen or an alkyl, a and b are numbers, mole %, the sum is less than 100; and wherein the copolymer is covalently linked to the surface-active moiety.

2. The composition according to claim 1, wherein the hydroxyethylpyrrolidone methacrylate/glycidyl methacrylate copolymer is covalently linked to a surface-active moiety, the composition having the structure:

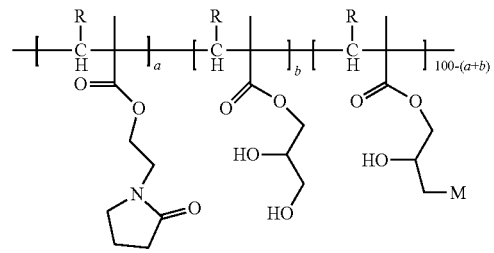

wherein R is hydrogen or an alkyl, a and b are numbers, mole %, the sum is less than 100;

and wherein M is the surface-active moiety.

3. The composition according to claim 1, wherein a and b are numbers, mole %, ranging from about 5 to about 95.

4. The composition according to claim 1, wherein the sum of a and b is a number, mole %, ranging from about 40 to about 99.99.

5. The composition according to claim 1, wherein the synthetic polymer of the semisynthetic moiety is prepared from at least one vinyl monomer selected from the group consisting of meth(acrylates), alkyl meth(acrylates), meth (acrylic acid), maleic anhydride, N-vinyl lactams, N-vinyl-2-pyrrolidone, N-vinylcaprolactam, styrene, acrylamide, alkyl acrylamides, 2-hydroxyethyl methacrylate and vinyl acetate.

6. The composition according to claim 1, wherein the modified allotrope moiety comprises a reactive functionality selected from the group consisting of —COOH, —OH, amine, amide, acid amides, imide, aldehydic, carbanion, thiol, epoxy, nitrile, oxetane, aziridine, isocyante, oxazoline, oxazine, phosphoric, sulfuric, sulfonic, boric, and combinations thereof.

7. A composition comprising:

I) about 0.1 wt. % to about 30 wt. % of:

A. a surface-active moiety covalently linked to a copolymer of hydroxyethylpyrrolidone methacrylate/glycidyl methacrylate, wherein the copolymer has the structure:

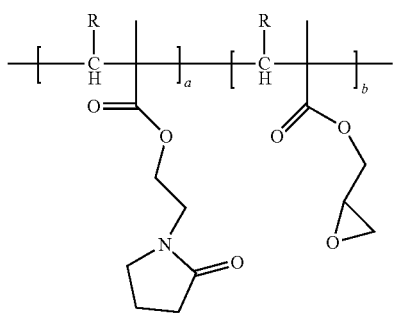

wherein R is hydrogen or an alkyl, a and b are mole %, the sum is less than 100; or B. a hydroxyethylpyrrolidone methacrylate/glycidyl methacrylate copolymer that is covalently linked to a surface-active moiety having the structure:

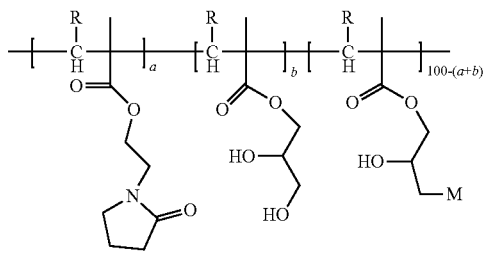

wherein R is hydrogen or an alkyl, a and b are numbers, mole %, the sum is less than 100; M is the surface-active moiety, and II) about 1.0 wt. % to about 99 wt. % of at least one additive;

wherein the surface-active moiety in either A. or B. is selected from the group consisting of:

a. organic moieties selected from the group consisting of:
i. natural moieties selected from the group consisting of biofunctional peptide, protein, glycolprotein, lipo-protein, polypeptide, DNA, RNA, and a pharmaceutical active, and/or ii. synthetic moieties selected from the group consisting of maleic anhydride-copolymer, itaconic anhydride copolymer, maleic acid-copolymer, itaconic acid-copolymer, polyterphtalate, polyalkyd, polyester, polyurethane, polyether, epoxy, nylon, poly(meth)acrylate, polyolefin, polyvinyl ether, polystyrene a pharmaceutical active, and a sunscreen active; and/or b. modified allotrope moieties selected from the group consisting of modified graphene, modified fullerenes, modified carbon nanotube, modified graphite, and modified carbon black.

8. The composition according to claim 7, wherein the additive is useful in an application selected from the group consisting of adhesives, aerosols, agricultural agents, anti-soil redeposition agents, batteries agents, beverages, biocides, cementing and construction agents, cleaning agents, coating agents, conductive materials, cosmetic agents, dental agents, decorated pigments, detergents, dispersants, drugs, electronics, encapsulations, foods, hair sprays, household-industrial institutional, inks and coatings, interlaminate adhesives, lithographic solutions, membrane additive agents, metal working fluids, oilfield agents, paints, paper, paper sizing agents, personal care agents, pharmaceuticals, pigment additives, plasters, plastic, printing, refractive index modifiers, sequestrants, soil release agents, static control agents and wood-care agents.

9. A composition comprising a cross-linked copolymer of hydroxyethylpyrrolidone methacrylate/glyceryl methacrylate covalently linked to one or more surface-active moiety having the structure:

(i)

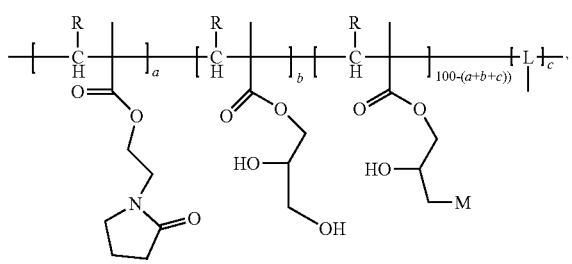

wherein R is hydrogen or an alkyl, a, b and c are numbers, mole %, the sum of which is less than 100, M is the surface-active moiety and L is difunctional moiety; or (ii)

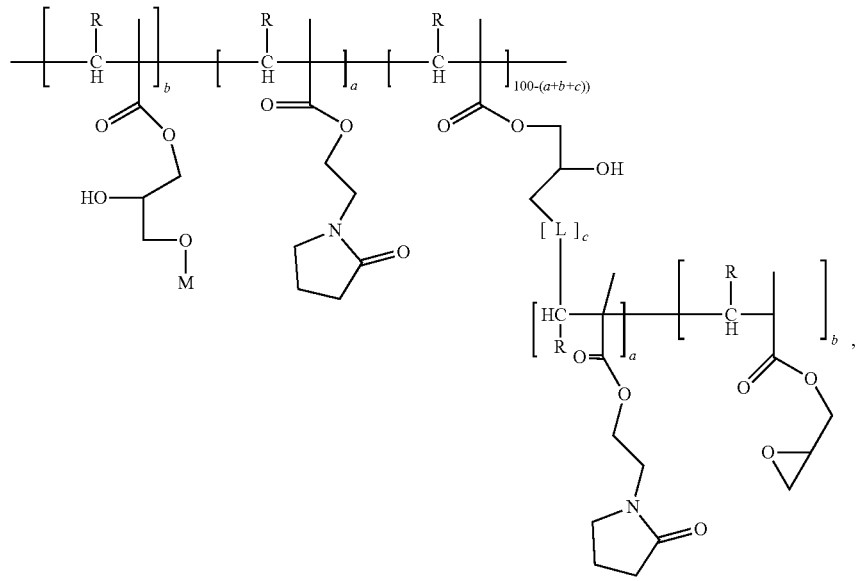

wherein R is hydrogen or an alkyl, a, b and c are numbers, mole %, the sum of which is less than 100, M is the surface-active moiety, L is a difunctional moiety;

wherein M of (i) or (ii) is selected from the group consisting of:

a. organic moieties selected from the group consisting of: natural moieties selected from the group consisting of a biofunctional peptide, protein, glycol-protein, lipo-protein, polypeptide, DNA, RNA, and a pharmaceutical active, synthetic moieties selected from the group consisting of maleic anhydride-copolymer, itaconic anhydride copolymer, maleic acid-copolymer, itaconic acid-copolymer, polyterphtalate, polyalkyd, polyester, polyurethane, polyether, epoxy, nylon, poly(meth)acrylate, polyolefin, polyvinyl ether, polystyrene, poly-vinyl-substituted-monomer, poly(meth)acrylamide, polyethyleneglycol, polypropyleneglycol, polysiloxane, polydimethylsiloxane, silicone polymer, polysulfone, polyamide, polylactam, a pharmaceutical active, a sunscreen active and; and/or b. modified allotrope moieties selected from the group consisting of modified graphene, modified fullerenes, modified carbon nanotube, modified graphite, and modified carbon black.

* * * * *